(12) United States Patent
Hao et al.

(10) Patent No.: US 11,253,171 B2
(45) Date of Patent: Feb. 22, 2022

(54) SYSTEM AND METHOD FOR PATIENT POSITIONING

(71) Applicant: SHANGHAI UNITED IMAGING HEALTHCARE CO., LTD., Shanghai (CN)

(72) Inventors: Weiqiang Hao, Shanghai (CN); Zhuobiao He, Shanghai (CN); Mingchao Wang, Shanghai (CN); Yining Wang, Shanghai (CN)

(73) Assignee: SHANGHAI UNITED IMAGING HEALTHCARE CO., LTD., Shanghai (CN)

(*) Notice: Subject to any disclaimer, the term of this patent is extended or adjusted under 35 U.S.C. 154(b) by 90 days.

(21) Appl. No.: 16/821,962

(22) Filed: Mar. 17, 2020

(65) Prior Publication Data
US 2020/0229737 A1 Jul. 23, 2020

Related U.S. Application Data

(63) Continuation of application No. 15/317,373, filed as application No. PCT/CN2016/075233 on Mar. 1, 2016, now Pat. No. 11,020,022.

(30) Foreign Application Priority Data

Mar. 2, 2015 (CN) .......................... 201510092839.7

(51) Int. Cl.
G06K 9/00 (2006.01)
A61B 5/11 (2006.01)
(Continued)

(52) U.S. Cl.
CPC .......... A61B 5/1114 (2013.01); A61B 5/0037 (2013.01); A61B 5/0077 (2013.01);
(Continued)

(58) Field of Classification Search
CPC ..... G06T 7/70; G06T 7/0012; G06T 2210/41; G06T 2207/30204; G06T 15/205;
(Continued)

(56) References Cited

U.S. PATENT DOCUMENTS 6,079,876 A 6/2000 Schuetz
6,724,922 B1 4/2004 Vilsmeier
(Continued)

FOREIGN PATENT DOCUMENTS

CN 202151380 U 2/2012
CN 103767722 A 5/2014
(Continued)

OTHER PUBLICATIONS

Timothy F. Cootes et al., Active Shape Models—Their Training and Application, Computer Vision and Image Understanding, 61(1): 38-59, 1995.
(Continued)

Primary Examiner — Guillermo M Rivera-Martinez
(74) Attorney, Agent, or Firm — Metis IP LLC

(57) ABSTRACT

The present disclosure relates to a positioning system suitable for use in an imaging system. The positioning system may include one or more cameras configured to capture images or videos of an imaging object and surrounding environment thereof for ROI targeting or patient position recognition. The positioning system may also include one or more position probes and sources configured to determine an instant location of an imaging object or an ROI thereof in a non-contact manner.

20 Claims, 16 Drawing Sheets

(51) Int. Cl.

| | |
|---|---|
| *A61B 6/04* | (2006.01) |
| *A61B 5/00* | (2006.01) |
| *A61B 5/055* | (2006.01) |
| *A61B 6/03* | (2006.01) |
| *A61B 90/00* | (2016.01) |
| *A61B 6/00* | (2006.01) |
| *A61B 8/08* | (2006.01) |
| *A61B 5/1495* | (2006.01) |
| *A61B 5/107* | (2006.01) |

(52) U.S. Cl.
CPC .............. *A61B 5/055* (2013.01); *A61B 6/032* (2013.01); *A61B 6/037* (2013.01); *A61B 6/04* (2013.01); *A61B 6/504* (2013.01); *A61B 8/08* (2013.01); *A61B 90/39* (2016.02); *A61B 5/0017* (2013.01); *A61B 5/1072* (2013.01); *A61B 5/1113* (2013.01); *A61B 5/1128* (2013.01); *A61B 5/1495* (2013.01); *A61B 5/742* (2013.01)

(58) Field of Classification Search
CPC .......... G06T 1/0007; G06K 2009/3291; G06K 9/00255; G06K 2209/05; G06K 2209/21; G06K 9/3233
See application file for complete search history.

(56) References Cited

U.S. PATENT DOCUMENTS

| | | | |
|---|---|---|---|
| 2001/0046316 A1 | 11/2001 | Miyano et al. | |
| 2002/0023652 A1* | 2/2002 | Riaziat ................ | A61N 5/1049 128/897 |
| 2002/0118280 A1 | 8/2002 | Medlar et al. | |
| 2002/0188194 A1 | 12/2002 | Cosman | |
| 2002/0193686 A1 | 12/2002 | Gilboa | |
| 2003/0130576 A1 | 7/2003 | Seeley et al. | |
| 2004/0015075 A1 | 1/2004 | Kimchy et al. | |
| 2004/0054248 A1 | 3/2004 | Kimchy et al. | |
| 2004/0081341 A1 | 4/2004 | Cherek et al. | |
| 2005/0256390 A1 | 11/2005 | Laux et al. | |
| 2005/0265516 A1 | 12/2005 | Haider | |
| 2007/0167801 A1 | 7/2007 | Webler et al. | |
| 2011/0178783 A1 | 7/2011 | Smith et al. | |
| 2011/0188726 A1 | 8/2011 | Nathaniel et al. | |
| 2012/0289825 A1* | 11/2012 | Rai ........................ | A61B 6/463 600/425 |
| 2013/0218024 A1 | 8/2013 | Boctor et al. | |
| 2013/0345718 A1 | 12/2013 | Crawford et al. | |
| 2014/0005484 A1 | 1/2014 | Charles | |
| 2014/0126699 A1 | 5/2014 | Lee | |
| 2014/0357989 A1 | 12/2014 | Hendriks et al. | |
| 2015/0051489 A1 | 2/2015 | Caluser et al. | |
| 2015/0062303 A1 | 3/2015 | Hanson et al. | |
| 2015/0157242 A1* | 6/2015 | Sabesan ................ | A61B 5/015 600/474 |
| 2015/0217137 A1* | 8/2015 | Takahashi ............ | A61N 5/1039 600/1 |
| 2016/0012390 A1 | 1/2016 | Skaaksrud | |
| 2016/0128666 A1 | 5/2016 | Grasruck et al. | |
| 2016/0166333 A1 | 6/2016 | Wang et al. | |
| 2016/0206203 A1 | 7/2016 | Yu et al. | |
| 2016/0324677 A1* | 11/2016 | Hyde ........................ | A61F 5/03 |
| 2017/0168124 A1 | 6/2017 | Ueda et al. | |
| 2017/0258526 A1 | 9/2017 | Lang | |
| 2018/0150960 A1* | 5/2018 | Derda .................... | A61B 90/36 |
| 2018/0270474 A1 | 9/2018 | Liu | |
| 2018/0325472 A1* | 11/2018 | Lin .......................... | A61B 6/04 |
| 2019/0046130 A1* | 2/2019 | Imamura ................ | A61B 6/464 |
| 2019/0183321 A1* | 6/2019 | Teranuma ................ | H04N 7/18 |
| 2019/0240508 A1* | 8/2019 | Friman ................ | A61N 5/1037 |
| 2019/0243138 A1* | 8/2019 | Peltola .................. | G16H 40/63 |
| 2019/0321657 A1 | 10/2019 | Hale | |
| 2020/0015911 A1* | 1/2020 | Yi .......................... | A61B 34/20 |
| 2020/0126272 A1 | 4/2020 | Baer-Beck et al. | |
| 2020/0218922 A1* | 7/2020 | Chen .................... | A61B 5/0022 |

FOREIGN PATENT DOCUMENTS

| | | |
|---|---|---|
| CN | 104000588 A | 8/2014 |
| CN | 104224212 A | 12/2014 |
| DE | 102007017794 B3 | 12/2008 |
| GB | 2340716 A | 2/2000 |
| WO | 2013160489 A1 | 10/2013 |
| WO | 2014120734 A1 | 8/2014 |
| WO | 2016138851 A1 | 9/2016 |

OTHER PUBLICATIONS

Timothy F. Cootes et al., Active Appearance Models, IEEE Transactions on Pattern Analysis and Machine Intelligence, 23(6): 681-685, 2001.
Olaf Ronneberger et al., U-Net: Convolutional Networks for Biomedical Image Segmentation, Medical Image Computing and Computer-Assisted Intervention, 9351: 234-241, 2015.
Communication Pursuant to Article 94(3)EPC in European Application No. 16758466.3 dated Feb. 25, 2021, 7 pages.
International Search Report in PCT/CN2016/075233 dated May 26, 2016, 5 pages.
Extended European Search Report in European Application No. 16758466.3 dated Jul. 25, 2018, 4 pages.

\* cited by examiner

700

SYSTEM AND METHOD FOR PATIENT POSITIONING

CROSS REFERENCE TO RELATED APPLICATIONS

This application is a continuation of U.S. patent application Ser. No. 15/317,373, filed on Dec. 8, 2016, which is a U.S. national stage under 35 U.S.C. § 371 of International Application No. PCT/CN2016/075233, filed on Mar. 1, 2016, designating the United States of America, which claims priority of Chinese Patent Application No. 201510092839.7 filed on Mar. 2, 2015, the contents of each of which are hereby incorporated by reference in its entirety.

TECHNICAL FIELD

The present invention relates to medical imaging, more particularly, the invention relates to a system and method for patient positioning during a medical imaging procedure.

BACKGROUND

Imaging systems, such as CT scanners, MRI scanners, PET scanners, are widely used for creating images of interior of a patient's body for medical diagnosis and/or treatment purposes. Generally, a region of interest (ROI) covering a portion of the patient's body, such as a limb or an internal organ, is selected before an imaging session starts. Data is then acquired from within the ROI and analyzed, giving swift and accurate diagnosis thereafter. Thus, to ensure high quality imaging and accurate diagnosis, the ROI must be properly targeted during imaging.

Patient positioning is an increasingly important consideration for medical imaging, of which application ranges from dental treatment to radiotherapy. Traditional patient positioning methods include the use of a laser pointer to mark the ROI on a patient's body, thereby allowing the imaging system to properly align with the patient.

However, some traditional positioning methods require human intervention, such as requiring a system operator to manually manipulate the laser for locating the ROI, which affects accuracy. Further, traditional positioning methods lack the feature for monitoring the ROI in real time. Thus, when the location of an ROI changes during an imaging session, such as due to body movement of the patient, the system cannot be easily adjusted to target the ROI properly.

Additionally, an imaging system usually need to know the patient position (e.g., whether the patient is lying in a prone or supine position) before an imaging session may be performed. Traditionally, a system operator may instruct a patient to take and maintain a particular patient position during an imaging session, and manually input that information for the imaging system to perform, such as choosing and executing a scanning protocol particularly designed for that patient position. When the patient position changes during an imaging session, such as mandated by the diagnosis or the patient's health condition, the operator may need to manually update the information before the imaging session may continue. Thus, the updating process again depends on human intervention, leaving room for human error. Further, the manual updating process sometimes consumes considerable amount of time, causing substantial delay and patient discomfort.

Thus, there exists a need for developing a new positioning method and system that is capable of real-time monitoring of a patient and accordingly adjusting an imaging system for any positional change with less or no human intervention. The new positioning system and method thus improve efficiency and accuracy of medical imaging.

SUMMARY OF THE INVENTION

In a first aspect of the present disclosure, provided herein is a positioning system. In some embodiments, the positioning system may include a position acquiring unit, a position processing unit, and a control unit. In some embodiments, the position acquiring unit may include one or more cameras. The camera(s) may be configured to monitor or communicate with an imaging object in real time. The position processing unit may be configured to process or analyze one or more images to produce an outcome. The control unit may be configured to generate control information based on the outcome. In some embodiments, the positioning system may be configured to compose a set of images and/or videos taken by the cameras in to a panoramic rendering of the imaging object and its surrounding environment.

In some embodiments, one or more images may include at least one characteristic feature indicative of a patient position and the positioning processing unit may be further configured to recognize the characteristic feature to determine the patient position.

In some embodiments, the control unit may be further configured to generate control information for defining an imaging protocol suitable for the patient position and may be capable of updating the control information pursuant to change of the patient position.

In some embodiments, one or more images may include at least one characteristic feature indicative of a region of interest (ROI) and the positioning processing unit may be further configured to recognize the characteristic feature to determine the ROI. In some embodiments, the control unit may be further configured to generate control information for targeting the ROI.

In some embodiments, the positioning processing unit may be further configured to calibrate the one or more images to generate a calibrated display and the control unit may be further configured to receive selection of a region of interest (ROI) from the calibrated display and generate control information for targeting the ROI.

In some embodiments, one or more images comprise at least one characteristic feature indicative of a reference position and the positioning processing unit may be further configured to recognize the characteristic feature to determine the reference position. In some embodiments, the control unit may be further configured to generate the control information based on the reference position.

In some embodiments, one or more cameras may have overlapping fields of view and the position processing unit may also further configured to compose the one or more images to generate a panoramic image.

In some embodiments, the positioning system may be configured to automatically recognize a patient position. In some embodiments, the positioning system may be configured to target a region of interest (ROI) on a patient's body on during an imaging session. In some embodiments, the ROI may cover an imaging object or a portion thereof. In some embodiments, the positioning system may be configured to communicate with an imaging system. In some embodiments, the positioning system may be configured to process patient's positional information, including but not limited to information regarding the patient position and the ROI, to generate control information. In some embodiments, the positioning system may send patient's positional information to the imaging system. In some embodiments, the positioning system may be configured to communicate with a hospital information system. In some embodiments, the positioning system may enable an operator of a imaging system to monitor a patient's status in real time.

In a second aspect of the present disclosure, provided herein is a positioning system, and the positioning system may include a position acquiring unit, a position processing unit, and a control unit. In some embodiments, the positioning system may include one or more position sources and position probes. The position source(s) and position probe(s) are used to monitor the instant location of an ROI. In some embodiments, the positioning system may be configured to determine a distance between a pair of position probe and position source based on communication between them. In some embodiments, ultrasound distance sensing may be used to determine the distance between a pair of position probe and position source.

In some embodiments, each position probe may have a communication range and be configured to terminate the non-contact communication of position probe(s) and source(s) when a position source leaves the communication range and to establish the non-contact communication when the position source enters the communication range of another position probe. In some embodiments, the non-contact communication may be conducted via ultrasound signaling.

In some embodiments, one or more position probes may include at least three position probes and the control unit may be further configured to execute control information.

In a third aspect of the present disclosure, provided herein is a method for positioning a patient for medical imaging. The method may include: obtaining one or more images of the patient; recognizing at least one characteristic marker from the images, the characteristic marker is indicative of a region of interest (ROI); generating control information based on the characteristic marker; positioning the patient based on the control information.

In some embodiments, the images may further include surrounding environment of the patient, and the at least one characteristic marker is located in the surrounding environment.

In a fourth aspect of the present disclosure, provided herein is a method for positioning a patient for medical imaging. The method may include: setting a position source indicative of region of interest (ROI) of the patient; establishing one or more position probes at known locations; measuring distances between the position source and the one or more position probes; calculating a location of the position source based on the measured distances; generating control information based on the calculated position of the position source; positioning the patient based on the control information.

In some embodiments, measuring distances between the position source and the one or more position probes may be performed by ultrasound distance sensing.

In some embodiments, the medical imaging used in the present disclosure may be selected from the group consisting of digital subtraction angiography (DSA), computed tomography (CT), computed tomography angiography (CTA), positron emission tomography (PET), X-ray imaging, magnetic resonance imaging (MRI), magnetic resonance angiography (MRA), single-photon emission computerized tomography (SPECT), ultrasound scanning (US), CT-MR, CT-PET, CE-SPECT, DSA-MR, PET-MR, PET-US, SPECT-US, transcranial magnetic stimulation (TMS)-MR, US-CT, US-MR, X-ray-CT, X-ray-MR, X-ray-portal, X-ray-US, Video-CT, and Vide-US.

DETAILED DESCRIPTION

The following description is presented to enable any person skilled in the art to make and use the invention, and is provided in the context of a particular application and its requirements. Various modifications to the disclosed embodiments will be readily apparent to those skilled in the art, and the general principles defined herein may be applied to other embodiments and applications without departing from the spirit and scope of the present invention. Thus, the present invention is not limited to the embodiments shown, but is to be accorded the widest scope consistent with the claims.

It will be understood that when a module or unit is referred to as being "on", "connected to" or "coupled to" another module or unit, it may be directly on, connected or coupled to the other module or unit or intervening module or unit may be present. In contrast, when a module or unit is referred to as being "directly on," "directly connected to" or "directly coupled to" another module or unit, there may be no intervening module or unit present. As used herein, the term "and/or" includes any and all combinations of one or more of the associated listed items.

The terminology used herein is for the purpose of describing particular example embodiments only and is not intended to be limiting. As used herein, the singular forms "a", "an" and "the" may be intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

Figure 1:
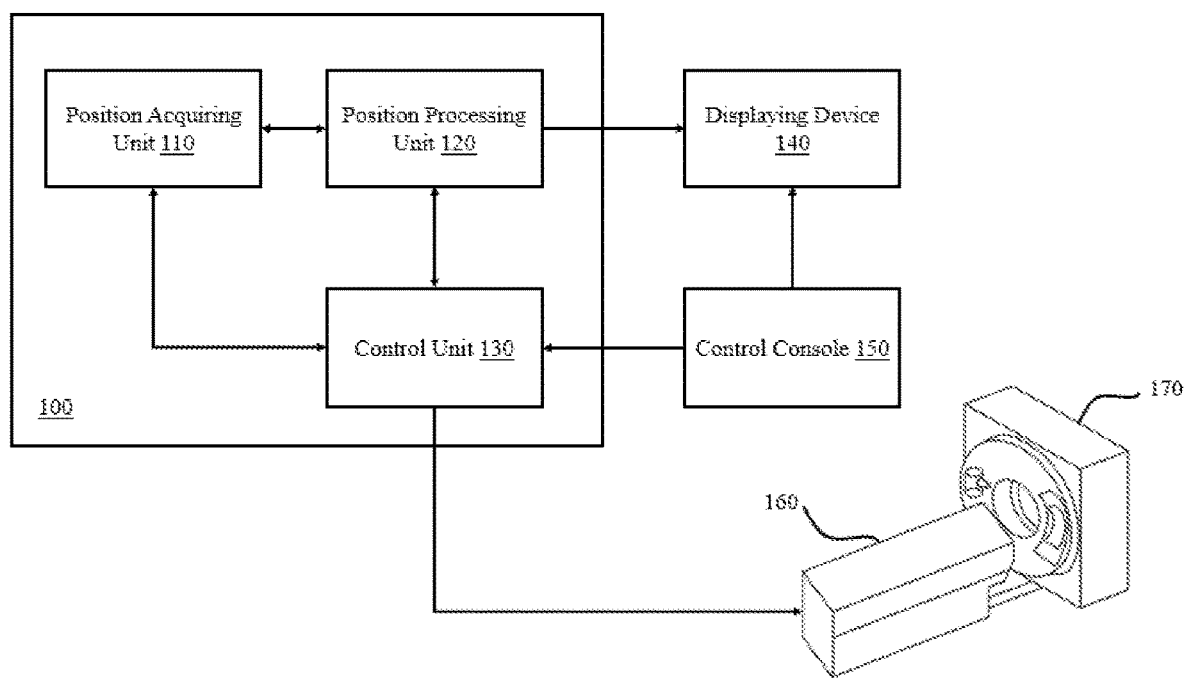
FIG. 1 illustrates an imaging system comprising a positioning system according to some embodiments of the present disclosure.

FIG. 1 illustrates an imaging system comprising a positioning system according to some embodiments of the present disclosure. In some embodiments, the positioning system 100 may be configured to automatically recognize a patient position. The term "patient position" as used herein refers to the physical positions of a patient's body, including the body's gesture, location within an imaging system, and orientation relative to components of the imaging system. For example, exemplary patient positions for a whole body scan include the supine, prone, right lateral recumbent, and left lateral recumbent positions. Further, in some embodiments, a patient position also includes information regarding the orientation of the body in the imaging system, such that the body is to be scanned in a certain direction, such as head to toe (e.g., head-first position), or toe to head (feet-first position).

In some embodiments, the positioning system 100 may be configured to target a region of interest (ROI) on a patient's body on during an imaging session. The term "region of interest" or "ROI" as used herein refers to a subset of an image, a video, or a dataset identified for a particular purpose. Particularly, images and videos include but are not limited to 2-dimensional image (2D), three-dimensional (3D), and four-dimensional (4D) ones, as well as those covering a narrow or a panoramic field of view. Datasets as used herein refers to sets of values of qualitative or quantities variables in any form, including but not limited to a digital, analog, or wave form. Exemplary embodiments of an ROI pertaining to the present disclosure include a time interval for data acquisition, a frequency interval for waveform data, a spatial region defined by boundaries on or within an object or a representation thereof, including but not limited to images or drawings illustrating the object's contours, surfaces or internal structures.

The term "target" as used herein refers to determining the ROI and/or acquiring data from within the ROI. Particularly, exemplary embodiments of targeting an ROI pertaining to the present disclosure include determining the ROI's form (e.g., a time interval or a spatial boundary), status (e.g., static or dynamic), location (e.g., in 3D space or on a 2D image), as well as positioning the ROI so as to acquire information from within the ROI (e.g., image or sound data).

In some embodiments, the ROI may cover an imaging object or a portion thereof. The term "imaging object" as used herein broadly relates to any organic or inorganic mass, natural or man-made, that has a chemical, biochemical, biological, physiological, biophysical and/or physical activity or function. Exemplary embodiments of an imaging object pertaining to the present disclosure include cells, tissues, organs or whole bodies of human or animal. Other exemplary embodiments include but not limited to man-made composition of organic and/or inorganic matters that are with or without life. In some embodiments, the imaging object may be a human patient. In some embodiments, the positioning system 100 may control the movement and positioning of an imaging object by controlling the movement of a support configured to carry the imaging object. In some embodiment the support is a patient support 160 that is a part of an imaging system 170.

In some embodiments, the positioning system 100 may be configured to communicate with an imaging system 170. Imaging systems that can be used in connection with the present disclosure include components and combinations of single-modality or multi-modality imaging systems and devices, some of which are used for non-invasive diagnosis, intervention and/or research in the biomedical field.

The term "imaging modality" or "modality" as used herein broadly refers to an imaging method or technology that gathers, generates, processes and/or analyzes imaging information of a target body through a particular mechanism. Accordingly, a multi-modality imaging system of the present disclosure can include more than one imaging modality, such as two, three, or more different modalities. In a multi-modality system, the mechanisms through which different imaging modalities operate or function can be the same or different. Accordingly, the imaging information can also be the same or different. For example, in some embodiments, the imaging information can be internal and/or external information, and can be functional and/or structural information of the target body. Particularly, in some embodiments, the imaging information of different modalities complement one another, thereby providing a set of imaging data describing a target body from different analytical angles. For example, in some embodiments, the multi-modality imaging achieves merging of morphological and functional images.

In various embodiments, the imaging system may comprise imaging modalities for conducting various different medical scans or studies, including but not limited to digital subtraction angiography (DSA), computed tomography (CT), computed tomography angiography (CTA), positron emission tomography (PET), X-ray, magnetic resonance imaging (MRI), magnetic resonance angiography (MRA), single-photon emission computerized tomography (SPECT), ultrasound scanning (US), ultrasound scan, bone densitometry, fluoroscopy. In various embodiments, exemplary multi-modality combination of the imaging system may include CT-MR, CT-PET, CE-SPECT, DSA-MR, PET-MR, PET-US, SPECT-US, TMS (transcranial magnetic stimulation)-MR, US-CT, US-MR, X-ray-CT, X-ray-MR, X-ray-portal, X-ray-US, Video-CT, Vide-US.

Particularly, in some embodiments, the positioning system 100 may be configured to process patient's positional information, including but not limited to information regarding the patient position and the ROI, to generate control information. The imaging system 170 then receives the control information and performs the positioning procedure accordingly.

In some embodiments, the positioning system 100 may send patient's positional information to the imaging system 170. The imaging system 170 then processes the patient's positional information to generate control information and performs the positioning procedure accordingly.

In some embodiments, the positioning system 100 may be configured to communicate with a hospital information system (HIS; not shown in the figure). As used herein, the term "hospital information system" or "HIS" refers to the whole or part of a comprehensive, integrated information system designed to manage all aspects of a hospital's operation, such as the hospital's medical, administrative, financial, and legal issues, and the corresponding processing of services. In some embodiments, the positioning system 100 may send patient's positional information or control information to the HIS. In some embodiments, the HIS may store and/or process information received from the positioning system 100. In some embodiments, the HIS may execute the control information to perform the positioning procedure. In some embodiments, the positioning system and/or the imaging system may be part of the HIS.

The term "control information" as used herein broadly relates to any information that directs operation of a system, including the positioning system and imaging system described herein. Exemplary embodiments of control information include information that specifies locations and/or directs movement of an ROI, an imaging object and/or one or more system components. In some embodiments, control information specifies a time, speed, path, angle and/or instruction for moving an ROI, an imaging object and/or one or more system components. In some embodiments, control information may be in the form of a machine-generated and/or user-input command that upon execution directs operation of the system, such as initiating a camera, running an algorithm, receiving, storing, or sending data, selecting an imaging protocol, and performing a positioning procedure etc. The term "positioning procedure" as used herein refers to the process of placing an imaging object in a particular physical position relative to an imaging system during the operation of the system.

In some embodiments, the positioning system 100 may enable an operator of the system to monitor a patient's status in real time. Particular, in some embodiments, the operator may input control information for the imaging system 170 to target a selected ROI. In some embodiment, an operator inputs control information via a console 150. In some embodiments, the positioning system 100 is configured to execute the control information. Particularly in some embodiments, the positioning system 100, upon receiving the control information, may move and position the imaging object and one or more components of the imaging system 170 relative to one another, such that the ROI is targeted in the corresponding imaging session.

In various embodiments, system components moved and positioned during the positioning procedure include but are not limited to a support (e.g., a patient bed, a handle etc.), a data acquisition device (e.g., an X-ray generator, a PET detector, etc.), a monitoring device (e.g., a camera, a lamp etc.), a communication device (e.g., a microphone, a keypad, etc.), and a mechanical part (e.g., for carrying the system components, for adjusting a patient position, etc.). In some embodiments, during the positioning procedure, the system sends voice instruction for a patient to perform. It should be noted that the above examples are provided for the purposes of illustration, and not intended to limit the scope of the present disclosure. After consulting the present disclosure, one skilled in the art may envisage numerous other changes, substitutions, variations, alterations, and modifications without inventive activity, and it is intended that the present disclosure encompasses all such changes, substitutions, variations, alterations, and modifications as falling within its scope.

Structure-wise, in some embodiments as shown in FIG. 1, the positioning system 100 may comprise a position acquiring unit 110. In some embodiments, the position acquiring unit 110 may include one or more cameras. In some embodiments, the camera(s) are used to monitor or communicate with an imaging object (such as a human patient) in real time. Particularly, in some embodiments, the camera(s) may be configured to capture images and/or videos of a patient near or in the imaging system 170. In some embodiments, the captured images and/or videos are used to monitor instant status of the patient, such as the patient's expression, gesture, and/or movement. In some embodiments, the captured images and/or videos are used for automatic patient position recognition. In some embodiments, the captured images and/or videos are used to assist ROI selection and targeting.

In some embodiments, multiple cameras may have a same or different field of view (FOV). For example, in some embodiments, one or more cameras may have a FOV covering a 90-180 degrees field. In some embodiments, one or more cameras may have a FOV covering 0-90 degrees field. In some embodiments, respective fields of view of multiple cameras may overlap.

In some embodiments, the positioning system 100 is configured to compose the set of images and/or videos taken by these cameras into a panoramic rendering of the imaging object and its surrounding environment. In some embodiments, the panorama is displayed to an operator of the system. As used herein, the term "panoramic" or "panorama" refers to an image or video that covers the maximum area of data acquisition of an imaging system, or an imaging object in its entirety, or an ROI in its entirety. In some embodiments, in addition to the imaging object or an ROI, a panorama also covers nearby environment where the imaging object or ROI is positioned. In some embodiments, a panorama has a field of view (FOV) of 0 to 45 degrees; in other embodiments, a panorama has a FOV of 45 to 90 degrees; in other embodiments, a panorama has a FOV of 90 to 180 degrees; in yet other embodiments, a panorama has a FOV of 180 to 360 degrees.

In some embodiments, the position acquiring unit 110 may comprise one or more position sources and probes. In some embodiments, the position source(s) and probe(s) are used to monitor the instant location of an ROI. Particularly, in some embodiments, the position sources and probes are configured to conduct non-contact communication. Particularly, in some embodiments, position sources may be configured to emit or receive a position signal, while position probes may be configured to receive or emit such position signal. In some embodiments, the position signal may be a non-contact signal of any form, including but not limited to optical signal, sound signal or magnetic signal. In some embodiments, a position source or a position probe may be placed on or near an ROI, thus the position signal may be used to determine the physical location of a ROI.

In some embodiments, the positioning system 100 is configured to determine a distance between of a pair of position probe and source based on communication between them. Particularly, in some embodiments, a position source's physical location in a three-dimensional space may be calculated based on its distance to one or more position probe(s) of known physical location in the three-dimensional space. The number of position probe(s) needed for the calculation depends on the relative spatial relationship between the source and the probe(s).

In some embodiments, ultrasound distance sensing may be used to determine the distance between a pair of position probe and source. For example, in some embodiments, a position source configured to emit an ultrasound signal is placed near an ROI, while one or more position probe(s) configured to receive the ultrasound signal are placed at known positions of the imaging system. The distance between the source and the probe(s) can be calculated based on the time delay between when the source emits the signal and when the probe receives it.

It should be noted that the implementation of ultrasound distance sensing is provided merely for the purposes of illustration, and not intended to limit the scope of the present disclosure. As would be appreciated by skilled person in the art, other mechanisms for non-contact distance sensing could also be used in connection with the present disclosure. For example, in some embodiments, infrared distance sensing and/or laser distance sensing may be used. In some embodiments, multiple distance sensing mechanisms may be used in combination.

In some embodiments, positional information obtained by the positing acquiring unit 110 is transmitted to be processed by a module external to the positioning system 100, such as by a processor of the imaging system or the HIS. In other embodiments, positional information is processed locally by the positioning system 100. As shown in FIG. 1, in some embodiments, the positioning system 100 comprises a stand-alone position processing unit 120 configured for receiving and processing the positional information. In other embodiments, a position processing unit 120 may be integrated with other modules of the positioning system 100. For example, in some embodiments, the position acquiring unit 110 and the position processing unit 120 may be an integrated unit.

In some embodiments, the position processing unit 120 is configured to analyze an image and/or video of an imaging object, such as a human patient. Particularly, in some embodiments, the position processing unit 120 is configured to recognize patient position based on the image and/or video. In some embodiments, the position processing unit 120 is configured to generate panoramic images and/or videos of an imaging object. In some embodiment, the position processing unit 120 is configured to target an ROI of an imaging object and generate control information. In some embodiments, the position processing unit 120 is configured to transmit processed positional information or control information to external modules, including but not limited a module of the positioning system 100, of the imaging system 170, or of an HIS.

According to the present disclosure, the position processing unit 120 may include any processor-based and/or microprocessor-based units. Merely by way of example, the processor may include a microcontroller, a reduced instruction set computer (RISC), application specific integrated circuits (ASICs), an application-specific instruction-set processor (ASIP), a central processing unit (CPU), a graphics processing unit (GPU), a physics processing unit (PPU), a microcontroller unit, a digital signal processor (DSP), a field programmable gate array (FPGA), an acorn reduced instruction set computing (RISC) machine (ARM), or any other circuit or processor capable of executing the functions described herein, or the like, or any combination thereof. The exemplary types of processors that may be used in connection with the present system are not exhaustive and are not limiting. After consulting the present disclosure, one skilled in the art may envisage numerous other changes, substitutions, variations, alterations, and modifications without inventive activity, and it is intended that the present disclosure encompasses all such changes, substitutions, variations, alterations, and modifications as falling within its scope.

As shown in FIG. 1, in some embodiments, the positioning system 100 may further comprise a stand-alone control unit 130 configured for receiving and executing control information to perform a positioning procedure. In other embodiments, a control unit 130 may be integrated with other modules of the positioning system 100, such as integrated with the position acquiring unit 110, the position processing unit 120 or both. In various embodiments, control information received and executed by the control unit 130 may include machine-generated information, such as control information generated by the positioning system 100, an imaging system or a HIS. Control information may also be input by a human operator of the system.

According to the present disclosure, the control unit 130 may include any processor-based and/or microprocessor-based units. Merely by way of example, the processor may include a microcontroller, a reduced instruction set computer (RISC), application specific integrated circuits (ASICs), an application-specific instruction-set processor (ASIP), a central processing unit (CPU), a graphics processing unit (GPU), a physics processing unit (PPU), a microcontroller unit, a digital signal processor (DSP), a field programmable gate array (FPGA), an acorn reduced instruction set computing (RISC) machine (ARM), or any other circuit or processor capable of executing the functions described herein, or the like, or any combination thereof. The exemplary types of processors that may be used in connection with the present system are not exhaustive and are not limiting. After consulting the present disclosure, one skilled in the art may envisage numerous other changes, substitutions, variations, alterations, and modifications without inventive activity, and it is intended that the present disclosure encompasses all such changes, substitutions, variations, alterations, and modifications as falling within its scope.

As shown in FIG. 1, in some embodiments, the positioning system 100 may further comprise one or more displaying devices 140. In some embodiments, the displaying device(s) 140 may be configured to display, among other things, patient's positional information acquired and/or processed by the positioning system 100. Further, in some embodiments, based on displayed information, a system operator may input control information for the imaging system to target a selected ROI.

According to the present disclosure, the displaying device 140 may be any suitable device that is capable of receiving, converting, processing, and/or displaying media content and/or performing any other suitable functions. For example, the display 140 can be and/or include a Liquid Crystal Display (LCD) panel, Organic Light Emitting Diodes (OLED), a cathode ray tube (CRT) display, a plasma display, a touch-screen display, a simulated touch screen, the like, or any combination thereof. In some embodiments, the display 140 may be capable of three-dimensional (3D) displaying. In some embodiments, the displaying device 140 can be implemented as a touchscreen configured to detect a touch input pressure, a touch input position, or the like, or any combination thereof.

As shown in FIG. 1, in some embodiments, the positioning system 100 may further comprise a console 150. In some embodiments, the console 150 may be any suitable input device that is capable of inputting information to the positioning system 100. Exemplary input devices may include but are not limited to a keyboard, a mouse, a touch screen, a voice controller, or the like, or any combination thereof.

It should be noted that the description of the positioning system is provided for the purposes of illustration, and not intended to limit the scope of the present disclosure. After consulting the present disclosure, one skilled in the art may envisage numerous other changes, substitutions, variations, alterations, and modifications without inventive activity, and it is intended that the present disclosure encompasses all such changes, substitutions, variations, alterations, and modifications as falling within its scope. For example, in some embodiments, the position processing unit 120 and the control unit 130 may be combined as a single unit.

Figure 2:
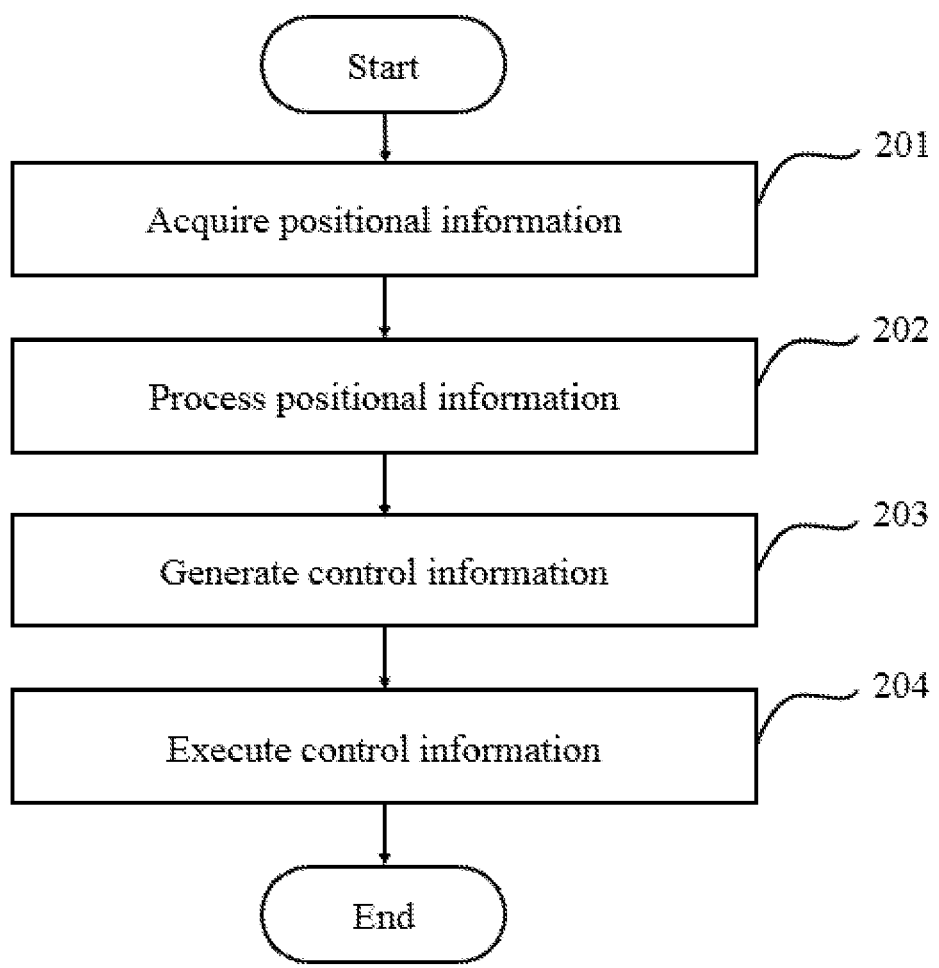
FIG. 2 is a flowchart illustrating a process performed by the present positioning system according to some embodiments of the present disclosure.

FIG. 2 is a flowchart illustrating a process performed by the present positioning system according to some embodiments of the present disclosure.

In step 201, positional information may be acquired. Exemplary mediums carrying the positional information may include images, videos, ultrasound, infrared beams, or any suitable medium for monitoring the status of a patient. Particularly, in some embodiments, the positioning system 100 comprises one or more cameras configured to monitor an imaging object and its surrounding environment. For example, in some embodiments, the cameras capture real-time images or videos of a patient lying on a patient support 160 of the imaging system 170.

In other embodiments, the positioning system 100 comprises pairing position sources and probes that are configured to communicate a position signal. For example, in some embodiments, one or more position sources are placed on a particular portion of a patient (e.g., near a ROI), and one or more position probes are placed at known locations. A position signal is transmitted between the position source(s) and position probe(s), thereby informing the positioning system 100 positional information of the imaging object. In various embodiments, the position signal may be ultrasound, infrared beams, or a combination thereof.

In step 202, positional information acquired in step 201 may be processed. In some embodiments, raw images and/or videos of an imaging object are processed. For example, in some embodiments, multiple cameras of the positioning system 100 are configured to each capture a portion of a patient's body. In step 202, the set of images and/or videos may be composed into a panoramic rendering for showing on the displaying device 140. The panorama covers the patient's full body and surrounding environment. In other embodiments, images of a patient may be analyzed for automatic recognition of the patient position. In yet other embodiments, the position signals transmitted between the position source and probe are analyzed to keep track of the instant location of an ROI.

In step 203, control information may be generated based on the positional information. The control information may include but is not limited to selection of an ROI for imaging and parameters for moving and positioning an imaging object and components of the imaging system such that the ROI can be properly targeted. For example, in some embodiments, an operator of the imaging system may manually set or update an ROI by selecting a portion on a displayed image. In other embodiments, the imaging system may automatically set or update the ROI, such as based on the recognized patient position. In other embodiments, an operator may manually input and/or the system may automatically generate various parameters for moving one or more system components (such as the patient support 160) to a suitable location, which parameters may include but are not limited to the distance, direction and speed of the movement. In yet other embodiments, an operator may manually input and/or the system may automatically generate or select protocols for controlling a subsequent imaging session, which parameters may include but are not limited to the method of image acquisition, duration, voltage, dosage, system components to be used in connection of the acquisition, and method of data processing, etc.

In step 204, the control information may be executed accordingly to perform a positioning procedure. For example, in a positioning procedure, an imaging object or one or more system components may be moved to a suitable location at a suitable speed. In various embodiments, system components moved and positioned during a positioning procedure include but are not limited to a support (e.g., a patient bed, a handle etc.), a data acquisition device (e.g., an X-ray generator, a PET detector, etc.), a monitoring device (e.g., a camera, a lamp etc.), a communication device (e.g., a microphone, a keypad, etc.), and a mechanical part (e.g., for carrying the system components, for adjusting a patient position, etc.). In some embodiments, during the positioning procedure, the system sends voice instruction for a patient to perform.

It should be noted that the flowchart above is provided for the purposes of illustration, and not intended to limit the scope of the present disclosure. After consulting the present disclosure, one skilled in the art may envisage numerous other changes, substitutions, variations, alterations, and modifications without inventive activity, and it is intended that the present disclosure encompasses all such changes, substitutions, variations, alterations, and modifications as falling within its scope.

Figure 3:
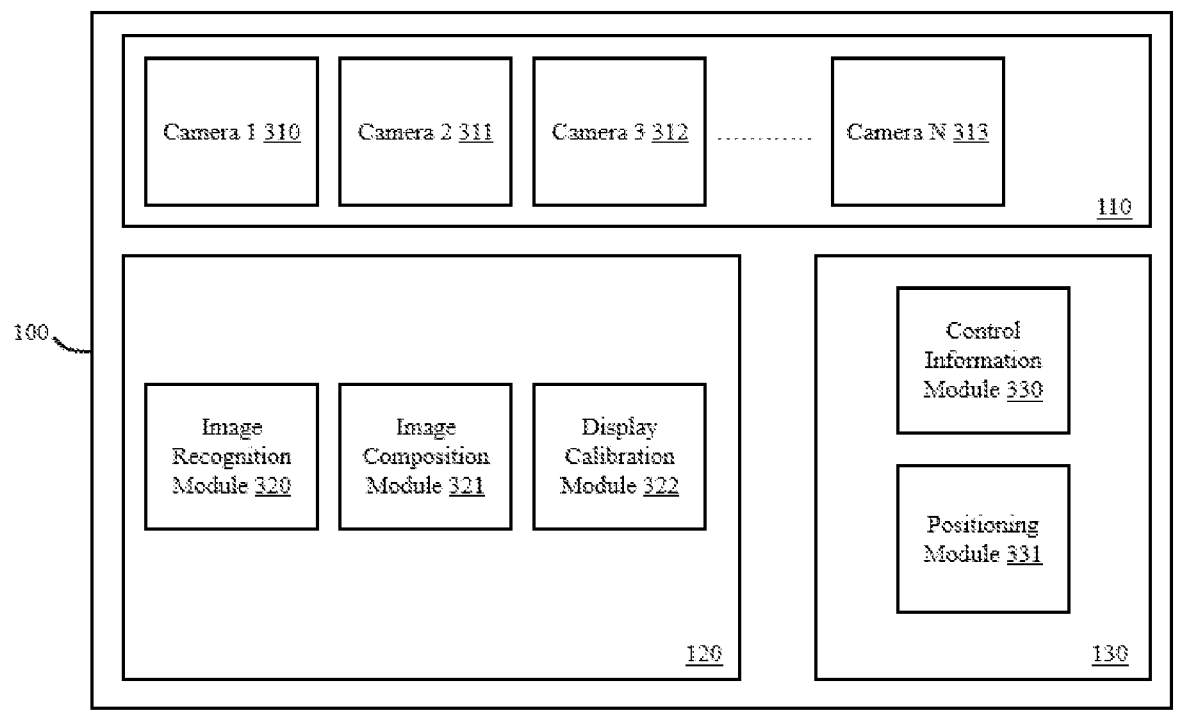
FIG. 3 is a block diagram of the positioning system according to some embodiments of the present disclosure.

FIG. 3 is a block diagram of the positioning system 100 according to some embodiments of the present disclosure. As shown in the figure, the positioning system 100 comprises a position acquiring unit 110, a position processing unit 120, and a control unit 130 as described in connection with FIG. 1 above.

Particularly, the position acquiring unit 110 may comprise one or more cameras for monitoring an imaging object. The cameras are labeled as camera 1 310, camera 2 311, camera 3 312, and camera N 313. The position processing unit 120 may comprise an image recognition module 320, an image composition module 321, and an image calibration module 322. The control unit 130 may comprise a control information module 330 and a positioning module 331.

According to the present disclosure, the camera(s) may be configured to monitor at least part of an imaging object and its surrounding environment. In some embodiments, the cameras may be mounted in the imaging gantry of an imaging system and configured to monitor a patient therein. Characteristics and setting of the camera(s) may vary according to a user's preference and practical needs. For example, if a medical practitioner needs to monitor a relatively small portion of a patient's body during an imaging session, such as the head or a limb, initiating a single camera of narrow FOV during the imaging session may suffice for the purpose. However, if a medical practitioner prefers to monitor the patient's entire body, a panoramic imaging solution may be used.

In some embodiment, the panoramic imaging solution may involve the use of a single camera, typically equipped with a wide to ultra-wide-angle lens. Exemplary wide-angle lenses include non-flat lenses and fisheye lenses. Selection of camera FOV involves a tradeoff between imaging coverage and quality. Particularly, as the camera FOV increases, the amount of imaging information and the size of a scene captured by the camera also increase. On the other hand, however, visual distortion also increases, as rendering the larger and larger amount of imaging information onto a flat image unavoidably requires more and more excessive stretching of pixels near borders of the image. The result is that produced panoramas may appear warped and do not correspond to a natural human view, which reduces authenticity and aesthetics of the image. In practice, flat panoramas start to look severely distorted once the camera FOV exceeds 90°. Thus, in some embodiments, the single-lens panoramic solution may be less preferred. Particularly, in those embodiments where the panoramic image is used for analyzing a patient position and/or positioning an imaging object or an ROI, visual distortion may negatively impact accuracy of the system.

An alternative solution is to use more cameras to cover a desirable total FOV, with each camera covering a smaller field without causing visual distortion. Thus, in some embodiments, the position acquiring unit 110 comprises a set of cameras. Particularly, each camera may be configured to capture at least part of a desired total FOV, such as an entire patient body and the patient support 160. Adjacent cameras' respective fields of view may overlap, such that the set of cameras together cover the desirable total FOV.

According to the present disclosure, the set of cameras may assume various different geometries as long as the captured set of images can be composed into a panorama covering a desirable total FOV. Particularly, the set of cameras may comprise any number of cameras. In some embodiments, the number of cameras may be greater than 1. Particularly in some embodiments, the number of cameras may range from 2 to 12. In some embodiments, the number of cameras may be any even number, such as 2, 4, 6, 8, 10, or 12 cameras. In some embodiments, the number of cameras may be any odd number, such as 3, 5, 7, 9, 10, or 11 cameras. Exemplary geometries of the camera set are described in details below in relation to FIGS. 5 and 6.

According to the present disclosure, camera(s) employed in the positioning system may be of various types and solutions. Exemplary cameras may include animation camera, autofocus camera, backup camera, banquet camera, box camera, bridge camera, camcorder, camera phone, closed-circuit television camera, compact camera, compact system cameras, dashcam, digital camera, disposable camera, document camera, field camera, firewire camera, folding camera, gun camera, helmet camera, high-speed camera, hidden camera, instant camera, IP camera, keychain camera, light-field camera, live-preview digital camera, medium format camera, mirrorless interchangeable-lens camera, monorail camera, movie camera, multiplane camera, omnidirectional camera, onboard camera, pinhole camera, pinspeck camera, plate camera, pocket camera, pocket video camera, point-and-shoot camera, pool safety camera, press camera, process camera, professional video camera, rapatronic camera, rangefinder camera, red light camera, reflex camera, remote camera, rostrum camera, schmidt camera, single-lens reflex camera, spy cam, spy camera, stat camera, stereo camera, still camera, still video camera, subminiature camera, system camera, thermal imaging camera (firefighting), thermographic camera, toy camera, traffic camera, traffic enforcement camera, twin-lens reflex camera, video camera, view camera, webcam, wright camera, zenith camera, zoom-lens reflex camera, or the like, or any combination thereof.

In some embodiments, the image composition module 321 may be configured to compose the set of images into a panoramic image. Depending on the geometry of how cameras are set around the imaging object and relative to one another, different image processing methods or algorithms may be used to generate the panorama. For example, in some embodiments, the imaging processing method registers set of images into alignment estimates, blends them in a seamless manner, and at the same time solves the potential problems such as blurring or ghosting caused by parallax and scene movements as well as varying image exposures. Particularly, in some embodiments, panorama composition may include registration, calibration and blending steps. Particularly, image registration may use the direct alignment method or the feature-based method to search for optimum alignments that minimize the sum of absolute differences between overlapping pixels of different images. Image calibration may be performed to minimize differences between an ideal lens model and the actual cameras and imaging condition, such as correcting optical defects, exposure differences, focus differences, vignetting, camera response, chromatic aberrations, blurring and ghosting etc. Image blending may be performed based on the result of image calibration, and combined with remapping of the images to an output projection.

In some embodiments, panorama composition may involve the direct alignment method and/or the feature-based method. Particularly, using the direct alignment method, each pixel of a first image may be compared with that of a second image, so as to find the optimum cut-and-stitch line for composing the two images. Using the feature-based method, features of the two images may be extracted and compared, so as to find the optimum cut-and-stitch line. Exemplary feature detecting and abstraction methods may include Harris, Scale-Invariant Feature Transform (SIFT), Speeded Up Robust Features (SURF), Features from Accelerated Segment Test (FAST), PCA-SIFT, and ORB techniques. In some embodiments, algorithms including mean square distance, least square, Euclidian distance, the linear weighted algorithm, Gaussian-weighted algorithm, may be used for panorama composition. Exemplary embodiments of panorama composition are described in details below in relation to FIGS. 7B and 7C.

In some embodiments, the display calibration module 322 may be configured to receive original images acquired by the position acquiring unit 110 or panoramic images generated by the image composition module 321, and further calibrate the images for displaying on a displaying device 140. Particularly, the display calibration module 322 registers positional information in physical space as corresponding positional information on a displayed image. Thus, when a system operator selects an ROI on a screen-displayed image, the positioning system 110 is able to translate the selection into a corresponding ROI in physical space. In some embodiments, the calibration may be based on a mapping relationship between the dimension of the panorama's total FOV and the dimension of the displayed image. An exemplary embodiment of the mapping relationship is described in details below in relation to FIG. 9.

In some embodiments, the image recognition module 320 may be configured to perform image-based automatic inspection and analysis for such applications as automatic patient position recognition and ROI targeting. Particularly, in some embodiments, the image recognition module 320 is configured to recognize one or more human body features from a captured image or video, the body feature(s) being indicative of the patient position. In some embodiments, the image recognition module 320 is configured to recognize one or more position markers from a captured image or video, the position marker(s) being indicative of the position of an ROI. Exemplary embodiments of image recognition are described in details below in relation to FIGS. 19 and 20.

In some embodiments, the control information module 330 may generate control information based on results transmitted from the position processing unit 120. In some embodiments, the control information module 330 may be configured to receive a system operator's input. In some embodiments, a calibrated panoramic image may be displayed on the displaying device 140. An operator of the imaging system may select an ROI on the displaying device 140 by manipulating the displayed panoramic image. For example, the operator may select the ROI by drawing a pair of lines or an area on the displayed image. The control information module 330 may receive the selection, translate the selection into parameters corresponding to the ROI's location in physical space, and generate a set of control information.

The positioning module 331 may be configured to receive and execute the control information. For example, in some embodiments, the positioning module 331 may execute the control information to perform a positioning procedure. Particularly, in some embodiments, the positioning module 331, upon receiving and executing the control information, may move a patient to the parameter-specified position in the imaging gantry, such that the ROI may be targeted during the next imaging session.

It should be noted that the above description of the positioning system is provided for the purposes of illustration, and not intended to limit the scope of the present disclosure. After consulting the present disclosure, one skilled in the art may envisage numerous other changes, substitutions, variations, alterations, and modifications without inventive activity, and it is intended that the present disclosure encompasses all such changes, substitutions, variations, alterations, and modifications as falling within its scope. For example, in some embodiments, the image recognition module 320, the image composition module 321 and the display calibration module 322 may be combined into a single functional unit.

Figure 4:
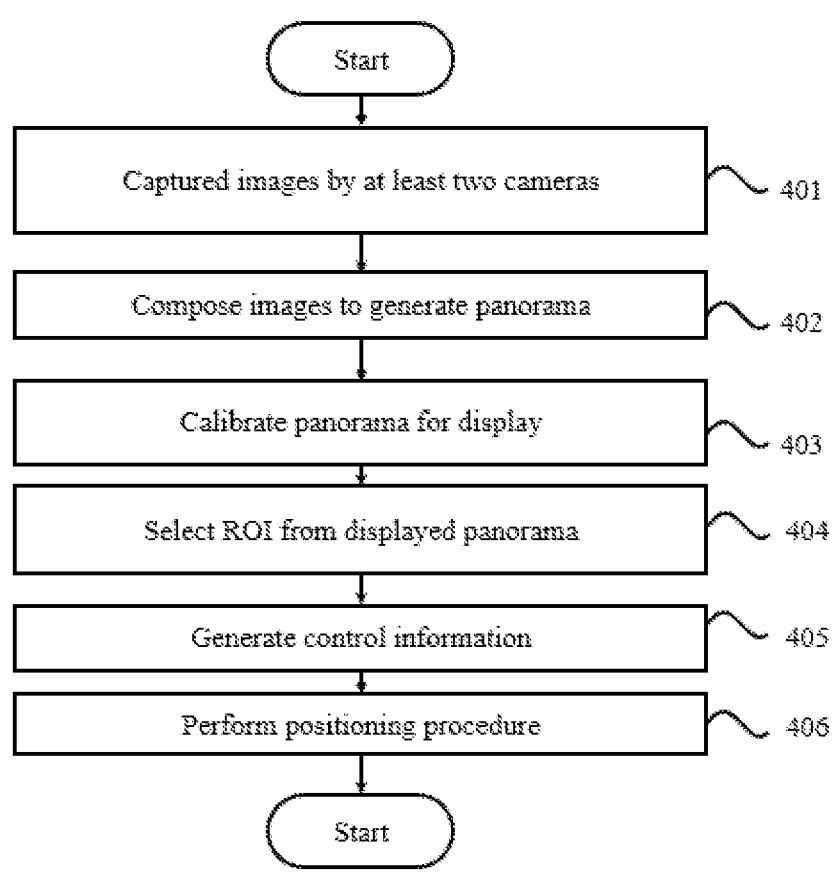
FIG. 4 is a flowchart illustrating an exemplary process of patient positioning according to some embodiments of the present disclosure.

FIG. 4 is a flowchart illustrating an exemplary process of patient positioning according to some embodiments of the present disclosure. In step 401, images captured by at least two cameras may be recognized. In some embodiments, each camera of the at least two cameras may be configured to monitor at least part of the imaging object. Two adjacent cameras of the at least two cameras may overlap in their respective FOV. In some embodiments, the cameras may be mounted inside an imaging gantry of an imaging system and configured to monitor a patient therein.

In step 402, images recognized in step 401 may be composed to generate a panoramic image that covers the entire imaging object and surrounding environment. Depending on the geometry of how cameras are set around the imaging object, different image-stitching algorithms may be used to generate the panorama.

In step 403, the panoramic image may be calibrated for displaying, such as on a displaying device 140 as described in connection with FIG. 1. The calibration algorithm registers positional information in physical space as corresponding positional information in the displayed image. Thus, when a system operator selects an ROI on a screen-displayed image, the system is able to translate the selection into a corresponding ROI in physical space. In some embodiments, the calibration may be based on a mapping relationship between the size of the panorama's total FOV and the size of the displayed image.

In step 404, an ROI may be selected based on the displayed panoramic image. In some embodiments, an operator of the imaging system may select an ROI either via the console 150 or directly on the displaying device 140 by manipulating the displayed panoramic image. For example, the operator may select the ROI by drawing a pair of lines or an area on the displayed image.

In step 405, control information may be generated based on the ROI selection in step 404. In the calibration step, the system keeps track of positional correspondence between the displayed image and the physical space. Thus, in some embodiments, after an ROI is selected, the system is able to translate the selection into parameters corresponding to the ROI's location in physical space, and generate a set of control information.

In step 406, positioning procedure may be performed. For example, in some embodiments, upon executing of the control information, the system may move a patient to the parameter-specified position in the imaging gantry, such that the ROI may be targeted during the next imaging session.

It should be noted that the above flowchart is provided for the purposes of illustration, and not intended to limit the scope of the present disclosure. After consulting the present disclosure, one skilled in the art may envisage numerous other changes, substitutions, variations, alterations, and modifications without inventive activity, and it is intended that the present disclosure encompasses all such changes, substitutions, variations, alterations, and modifications as falling within its scope.

Figure 5:
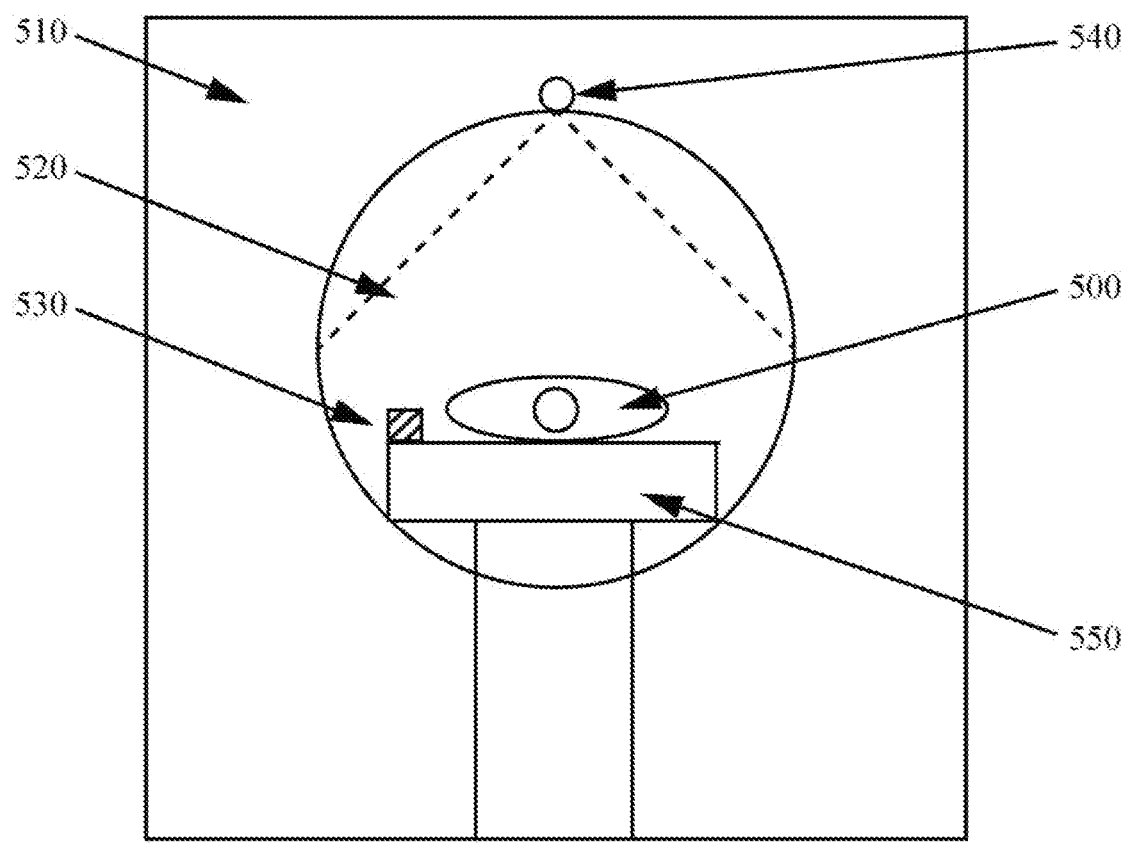
FIG. 5 is a schematic illustration of a cross-sectional view of the imaging system according to some embodiments of the present disclosure.
Figure 6:
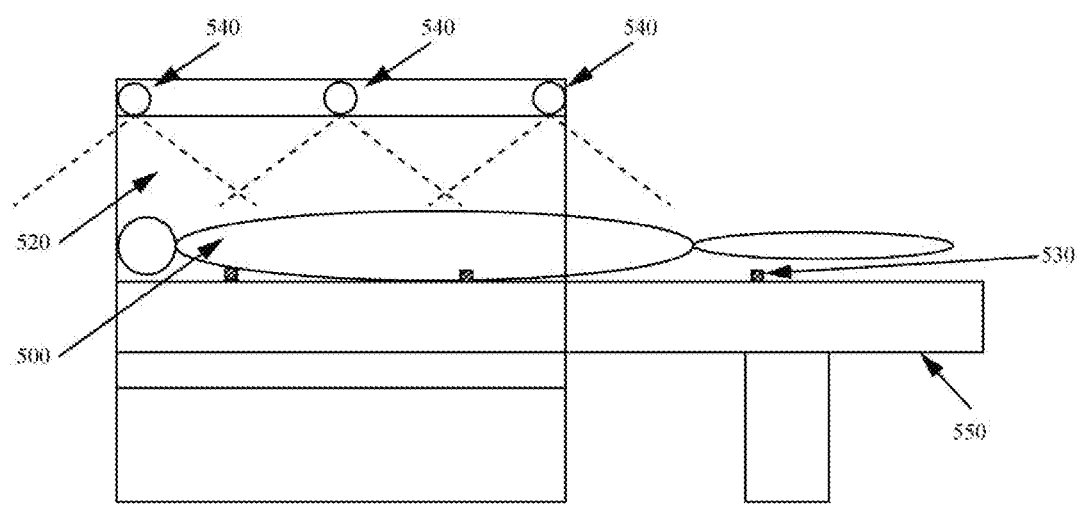
FIG. 6 is a schematic illustration of a side view of the imaging system according to some embodiments of the present disclosure.

FIGS. 5 and 6 illustrate exemplary embodiments of an imaging device equipped with a positioning system according to the present disclosure.

Particularly, FIG. 5 is a schematic illustration of a cross-sectional view of the imaging system according to some embodiments of the present disclosure. As can be seen from this view, a patient 500 lies on a patient support 550. The patient support 550 is configured to move the patient 500 in and out of an imaging gantry 520 of an imaging system 510. One or more reference pattern 530 is placed on the patient support 550. One or more camera 540 is placed in the imaging gantry 520 above the centerline of the patient's body.

FIG. 6 is a schematic illustration of a side view of the imaging system according to some embodiments of the present disclosure. As can be seen from this view, three cameras 540 are mounted inside the imaging gantry 520. A patient 500 is lying on the patient support 550. The cameras are arranged in a straight line above the center of the patient's body. Two adjacent cameras have an overlapping area in their respective FOV. Three reference patterns 530 are placed on the patient support 550.

In this particular embodiment, the three cameras 540 are mounted at the same vertical height from the patient support 550 and are arranged in a straight line with respect to one another. Particularly, the straight line may be parallel with the longitudinal axis of the patient support 550 moves. In some embodiments, the straight line may superimpose with the centerline of the patient's body 500; that is, the cameras 540 are mounted above the center of the patient's body 500. In some embodiments, the cameras 540 are distributed evenly in a straight line; that is, distances between adjacent cameras 540 are the same.

However, it can be now appreciated that a variety of embodiments of the position acquiring unit 110 may be employed. These embodiments may have different numbers and/or arrangements of cameras, but a common feature is that each camera's FOV overlaps with that of at least one other camera, thereby enabling the positioning system 100 to capture a desirable total FOV. Those of ordinary skills in the art upon reading the present disclosure should become aware of how a position acquiring unit according to the present disclosure can be designed to satisfy particular needs. Particularly, skilled persons in the art would follow the guidance provided by the present disclosure to select a suitable number of cameras with reasonable fields of view and arrange the set of cameras such that neighboring cameras' fields of view have reasonable overlap that enables the system to cover a desirable total FOV and reliably process image information in the overlapping field to produce panoramas. Some exemplary geometries of the set of camera that may be employed are described further below.

Particularly, in some embodiments, the number of cameras may be less or more than 3. For example, in some embodiments, the system includes two or more lines of cameras aligned above a scanning area. Each line of cameras may or may not superimpose with the centerline of the scanning area. In some embodiments, overlapping FOV exists for adjacent cameras in the same line and/or in different lines.

In some embodiments, the cameras may not align in a straight line with respect to one another. For example, in some embodiments, the cameras may be scattered around an imaging object. In some embodiments, the set of cameras may be arranged in a curve or in a convex or concave surface, such as on the surface of a sphere.

In some embodiments, the cameras may not sit at the same vertical height from a reference plane, such as the patient support. For example, one camera may be placed at a lower position than other cameras, due to spatial constraint in the imaging gantry. In some embodiments, distances between adjacent cameras may not be the same. Particularly, in some embodiments, overlapping area of different pairs of adjacent cameras may be of different size.

In some embodiments, camera FOV may range between 20° to 90°, such as 20°, 30°, 40°, 50°, 60°, 70°, 80° and 90°. In some embodiments, camera FOV may be greater than 90°, such as 90°, 100°, 110°, 120°, 130°, 140°, 150°, 160°, 170°, and 180°.

Depending on the geometry of how cameras are set around the imaging object, different image-stitching algorithms may be used to generate the panorama. In the embodiments as shown in FIGS. 5 and 6, reference patterns are used to help locating the overlapping areas in adjacent images. Particularly, one or more characteristic reference patterns may be placed in the overlapping FOV of adjacent cameras. These reference patterns thus are indicative of the physical range covered by a given camera, as well as an overlapping area that is captured in both adjacent images. Thus, based on the location of a reference pattern, adjacent images may be cut and stitched along the edge of the overlapping area to form a continuous image covering a larger total FOV.

Figure 7A:
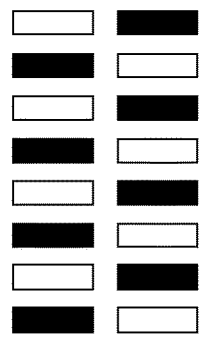
FIG. 7A illustrates an exemplary embodiment of a reference pattern that may be employed in the positioning system according to some embodiments of the present disclosure.

The reference pattern may have any combination of colors, shapes, and/or textures, including but not limited to black, white, gray scale, colorful, fluorescent; standard geometrical shapes such as circle, oval, triangle, square, trapezium, diamond, rhombus, parallelogram, rectangle, pentagon, hexagon, heptagon, oblong, octagon, nonagon, decagon or the like; symbols such as star, heart, moon, arrow, stripe, ladder or the like; icons or images such as a teddy bear, a national flag or the like; letters, barcodes and characters; textures such as rough, smooth, heat-absorbing, heat-reflective, etc. Merely by way of example, FIG. 7A illustrates an exemplary embodiment of a reference pattern that may be employed in the positioning system according to some embodiments of the present disclosure. As shown in the figure, the reference pattern 700 comprises two columns of alternating black and white boxes.

In some embodiments, the reference patterns may be placed on the patient support. In other embodiments, the reference patterns may be placed in the coils of an MRI scanner.

Figure 7B:
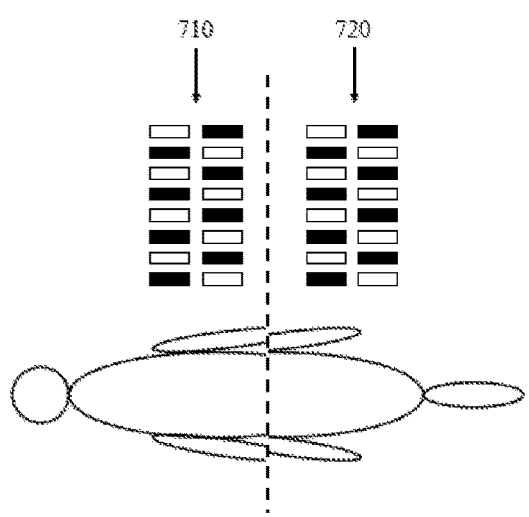
FIGS. 7B and 7C illustrate an exemplary method for panorama composition.
Figure 7C:
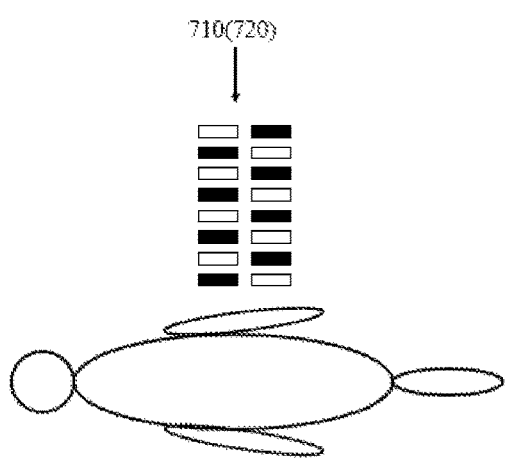

FIGS. 7B and 7C illustrate an exemplary method for panorama composition. Particularly, FIG. 7B shows a pair of adjacent images having an overlapping FOV. Both images capture the reference pattern in the overlapping FOV (710, 720). To find an optimum cutting-and-stitching line for composing the pair of image, the method first aligns the two images to the extent that the reference patterns (710, 720) as in the two images overlap completely. Then the overlapped area in one of the two images may be cut and the remaining portions of the images may be stitched together to produce the panorama as shown in FIG. 7C.

Figure 8:
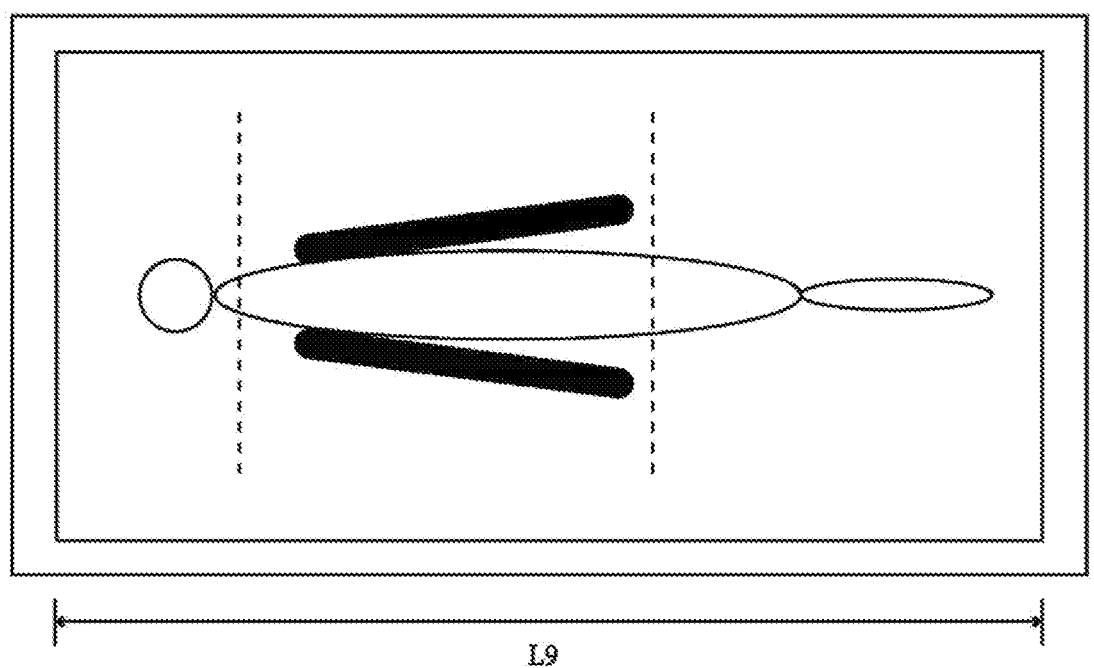
FIG. 8 illustrates a displaying device showing a calibrated panoramic image according to some embodiments of the present disclosure.

FIG. 8 illustrates a displaying device showing a calibrated panoramic image according to some embodiments of the present disclosure. As shown in the figure, a calibrated panoramic image may be shown on a display 800. In various embodiments, the display 800 may be embodied as a touch screen, or other suitable displaying devices. In this figure, L9 denotes a dimension of the displayed panorama.

An operator of the imaging system may select an ROI directly from the calibrated panoramic image by manipulating the touch screen 800. In this particular embodiment, the operator draws a pair of lines flanking part of the patient's body as the ROI. In some embodiments, the operator may select an ROI via an input device, such as a keyboard or a mouse. In some embodiments, a rotary knob may be employed for fine adjustment of the position of the ROI selected by the operator. In some embodiments, the input devices may be integrated on the console 150 as described in connection with FIG. 1. It should be noted that the calibrated panoramic image described above is provided for the purposes of illustration, and not intended to limit the scope of the present disclosure. After consulting the present disclosure, one skilled in the art may envisage numerous other changes, substitutions, variations, alterations, and modifications without inventive activity, and it is intended that the present disclosure encompasses all such changes, substitutions, variations, alterations, and modifications as falling within its scope.

Figure 9:
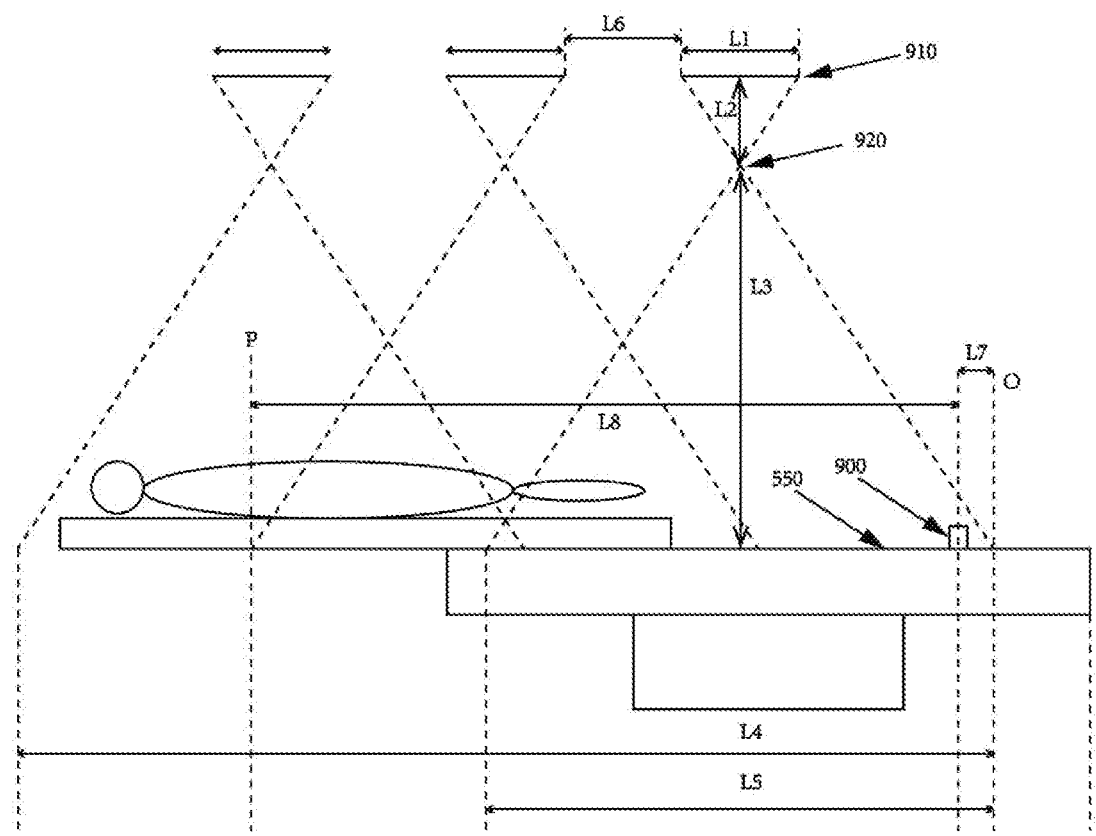
FIG. 9 illustrates exemplary procedures for calibrating an image and generating control information according to some embodiments of the present disclosure.

FIG. 9 illustrates exemplary procedures for calibrating an image and generating control information according to some embodiments of the present disclosure. Particularly, the image may be a single camera image or multi-camera panorama.

In the embodiment shown in FIG. 9, the positioning system comprises multiple cameras having overlapping fields of view. Each camera may comprise an image sensor 910 and a lens 920. The cameras are mounted above the patient support 550 at the same height, and the cameras are arranged in a straight line. The straight line is parallel with the longitudinal axis of the patient support 550.

As shown in the figure, L1 denotes a dimension of the image sensor 910. L2 denotes the distance between the image sensor 910 and the lens 920. L3 denotes the distance between the lens 920 and the captured scene (for example, the patient support 550). L5 denotes a dimension of the captured FOV, which may change with L3. L6 denotes the distance between adjacent cameras. In this configuration, a ratio between the dimension of the image sensor 910 (L1) and the dimension of the captured FOV (L5) is L2/L3. Thus, L5 can be calculated as:

$$L5 = L1 * L3/L2 \quad \text{(Equation 1)}$$

In some embodiments, calibrating the image for displaying may be based on a mapping relationship between the dimension of the captured FOV (L5) and the dimension of the displayed image (L9 as shown in FIG. 8). Particularly, the mapping relationship can be written as the ratio: L9/L5.

Optionally, the system of FIG. 9 may perform panoramic imaging using multiple cameras. Let N denote the number of cameras used in the panoramic imaging solution, and L4 denote a dimension of the total panoramic FOV. In this configuration, L4 can be calculated as:

$$L4 = L5 + (N-1)*L6 + (N-1)*L1 \quad \text{(Equation 2)}$$

Accordingly, the mapping relationship for calibrating the multi-camera panoramic image for displaying can be written as the ratio: L9/L4.

The dimension of the displayed image (L9) correlates with the size of an area used for displaying the image, such as on a screen. In some embodiments, a system operator may customize the displaying area, such as having the image displayed in full screen, or enlarged to display in extended double screens, or reduced to display in a half-screen window. Thus, the mapping relationship may remain constant or change during operation of the imaging system. In any case, the display calibration module 322 of the positioning system 100 keeps track of the instant mapping relationship during calibration.

As such, the calibration process registers positional information in physical space (e.g., L4) as corresponding positional information in the displayed image (e.g., L9). Thus, when an operator specifies a particular region of the displayed patient's body as the ROI, the positioning system is able to calculate the corresponding region in physical space, and generate control information for moving and/or positioning various components of the imaging system, including but not limited to the patient support 550, such that the corresponding physical region will be properly targeted during imaging.

For example, in the embodiment as shown in FIG. 9, the operator draws line P on the displayed image, which denotes the position where the scan should begin or end. To calculate the physical position of line P, in some embodiment, zero position 900 of known physical position is used as a reference point. Particularly, in some embodiment, zero position 900 is provided as a marker on the patient support 550. In some embodiments, a reference pattern may be used to denote zero position 900.

In some embodiments, height of the patient support 550 is adjusted such that zero position 900 is within the total panoramic FOV, and thus is shown on the displayed image. Particularly, in the embodiment as shown in FIG. 9, line O denotes the edge of the total panoramic FOV that covers zero position 900. As shown in the figure, L7 denotes the physical distance between edge O and the zero position 900, and L8 denotes the physical distance between line P and zero position 900. Let L8' (not shown in the figure) denotes the displayed distance between line P and zero position 900. According to the mapping relationship described above, $$L8'/L8 = L9/L4 \quad \text{(Equation 3)}$$

As described above, the mapping relationship (L9/L4) and the displayed distance (L8') are known to the positioning system. Thus, the physical distance between line P and zero position 900 (L8) can be calculated. Further, because zero position 900 is known, the physical position of line P can be obtained.

Figure 10:
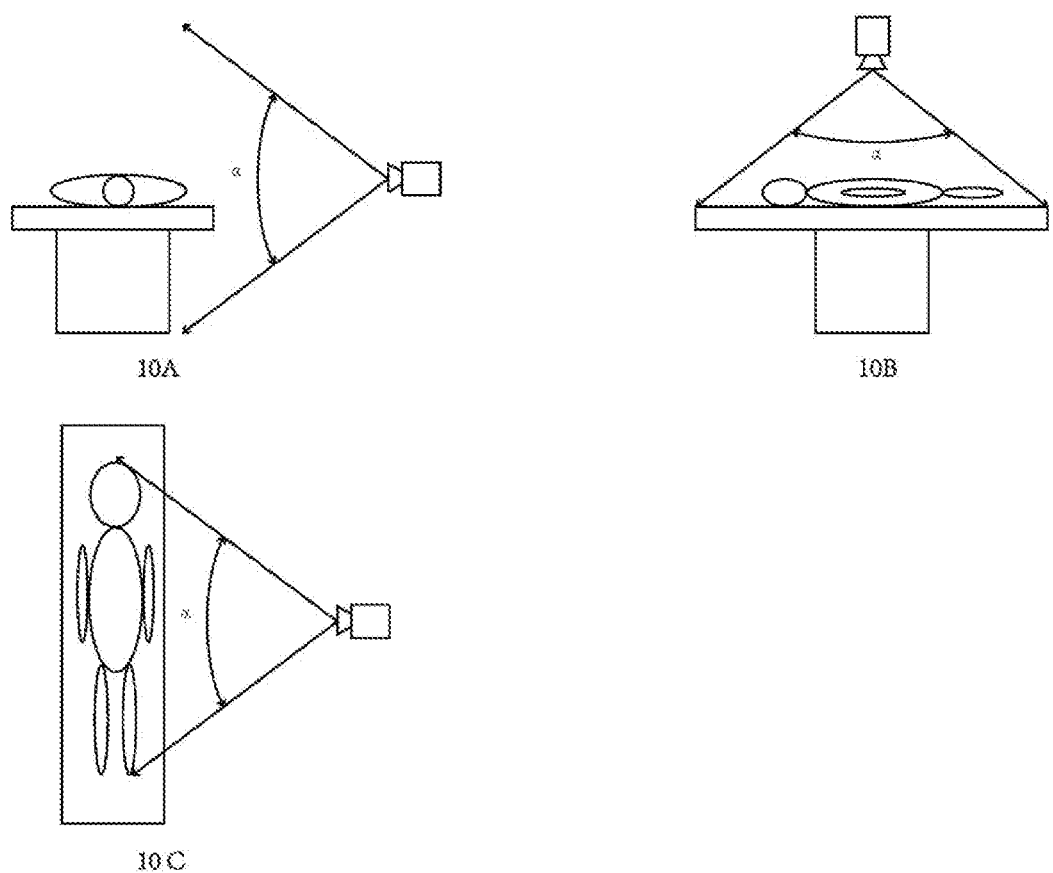
FIGS. 10A through 10C illustrate exemplary locations of one or more cameras capturing a patient lying on a patient support according to the several embodiments of the present disclosure.
Figure 11:
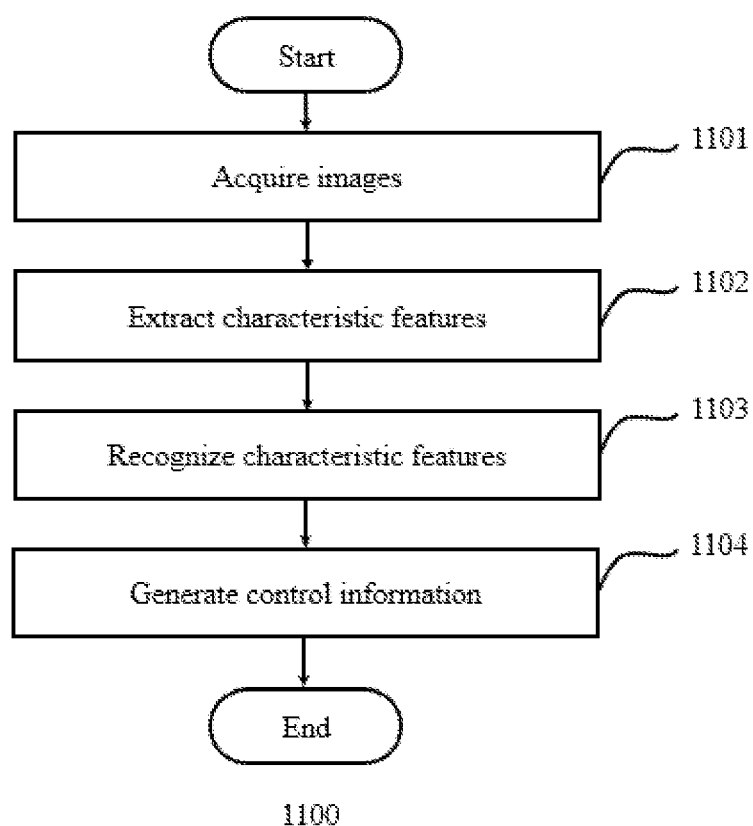
FIG. 11 illustrates an exemplary process of image recognition according to some embodiments of the present disclosure.

FIGS. 10 and 11 illustrate exemplary system components and procedure for image recognition according to several embodiments of the present disclosure. Depending on practical needs or user preferences, in various embodiments, the image and/or video for image recognition may be taken from various angles with respect to the imaging object; may cover the entire imaging object or certain feature-containing portions; may be a panoramic rendering or a narrow FOV rendering of the imaging object; and may be in 2D or 3D. For example, FIGS. 10A through 10C illustrate exemplary locations of one or more cameras capturing a patient lying on a patient support according to the several embodiments of the present disclosure. As shown in the figure, the camera may be placed at various locations and angles with respect to the patient. For example, as shown in FIG. 10A, a camera may be placed lateral to the patient support and captures a FOV (a) that covers the vertical dimension of the patient. As shown in FIG. 10B, a camera may be placed above the patient support captures a FOV (a) that covers the horizontal dimension of the patient. As shown in FIG. 10C, the camera may be installed lateral to the patient support and captures a FOV (a) that covers the horizontal dimension of the patient. In some embodiments, these cameras may be initiated simultaneously or sequentially during image recognition. In some embodiments, one or more cameras may be only installed within a space where imaging takes place, such as installed inside an imaging gantry. Thus, the cameras are capable of monitoring and updating a patient's instant status during an imaging session.

FIG. 11 illustrates an exemplary process of image recognition according to some embodiments of the present disclosure. The method or process 1100 may be performed by processing logic that comprises hardware (e.g., cameras, patient support, circuitry, dedicated logic, programmable logic, microcode, etc.), software (e.g., instructions run on a processing device to perform hardware simulation), or a combination thereof. In some embodiments, one or more operations of the method 1100 can be performed by one or more computing and/or console devices (e.g., one or more computing and/or console devices as described above in connection with FIG. 1) to generate and execute control information automatically.

In step 1101, one or more images and/or videos of a patient assuming a patient position may be acquired. Depending on practical need or user preference, the one or more images and/or videos may be taken from different angles with respect to the patient; may cover the patient's entire body or certain feature-containing portions of the body, such as face, limbs, back or chest.

In step 1102, characteristic features in the images are extracted. Pertaining to the present disclosure, characteristic features may include features of an imaging object itself and features in the surrounding environment of an imaging object.

Particularly, in some embodiments, characteristic features include human body features, such as facial features (e.g., eye or nose), body features (e.g., limb or chest), gender features (e.g., breast or laryngeal prominence), morphology features (e.g., lesion or tumor), gesture features (e.g., prone or supine), orientation features (e.g., head-first or feet-first), and behavior features (e.g., move or turn). One or more of these body features are indicative of the patient position, such as but not limited to a head-first supine position, a feet-first prone position, a head-first left lateral recumbent position or a feet-first right lateral recumbent position, etc.

In some embodiments, characteristic features include position markers placed on or near an imaging object. Particularly, in some embodiments, position markers may be placed on the patient support or other system components. In some embodiments, system components of distinctive exterior features may serve as positional markers, such as a coil or other accessories of the system. According to the present disclosure, position markers may be of any distinctive combination of shape, color and/or texture. Exemplary embodiments include black, white, gray scale, colorful, fluorescent; standard geometrical shapes such as circle, oval, triangle, square, trapezium, diamond, rhombus, parallelogram, rectangle, pentagon, hexagon, heptagon, oblong, octagon, nonagon, decagon or the like; symbols such as star, heart, moon, arrow, stripe, ladder or the like; icons or images such as a teddy bear, a national flag or the like; letters, barcodes and characters; textures such as rough, smooth, heat-absorbing, heat-reflective, etc.

Characteristic features captured on camera may be recognized due to their characteristic color, shape, texture, spatial relationship or any combination thereof. Various methods or algorithms may be used. For shape extraction, methods or algorithms that can be used include multi-scale edge detection, wavelets and Chamfer matching, low level feature selection, feature extraction by shape matching, flexible shape extraction, LBP, GLDM, GLRLM, Haralick and Gabor texture features. For color extraction, methods or algorithms that can be used include color-histogram, color sets, color matrix. For texture extraction, methods or algorithms that can be used include structural approach, signal processing method, geometric method, model technique, statistical technique. Special relationship extraction can be performed by extracting features after segmenting images either according to colors or targets in the images or segmenting images into several regular slave modules. Methods or algorithms that can be used in connection with the present disclosure also include other machine vision algorithms currently available or to be developed in the future.

In step 1103, characteristic features are recognized. Various methods or algorithms may be used. For example, in some embodiments, an extracted feature is compared to a pre-stored reference feature for a match. If a match is found, the extracted feature is recognized and related information is recorded; otherwise, the extracted feature is ignored. Exemplary embodiments of algorithms that can be used in connection with the present disclosure include Principal component analysis using eigenfaces, Linear discriminate analysis, Elastic bunch graph matching using the fisherface algorithm, the hidden Markov model, the multilinear subspace learning using tensor representation, the neuronal motivated dynamic link matching, 3D model-based algorithms, recognition, skin texture analysis, thermal cameras, skeletal-based algorithms, appearance-based models, or other methods currently available or to be developed in the future.

In step 1104, control information is generated according to the recognized characteristic features. The control information may be automatically generated by a system or input by a system operator based on the result of imaging recognition. For example, in some embodiments, a system is configured to automatically select a particular imaging protocol based on a recognized patient position. In some embodiments, the system is configured to display the result of image recognition for a system operator to input control information. In some embodiments, generated control information is executed locally by the positioning system. In other embodiments, generated control information is transmitted to a system external to the positioning system (such as an imaging system or a HIS) for execution.

It should be noted that the above embodiments are provided for the purposes of illustration, and not intended to limit the scope of the present disclosure. After consulting the present disclosure, one skilled in the art may envisage numerous other changes, substitutions, variations, alterations, and modifications without inventive activity, and it is intended that the present disclosure encompasses all such changes, substitutions, variations, alterations, and modifications as falling within its scope.

Figure 12:
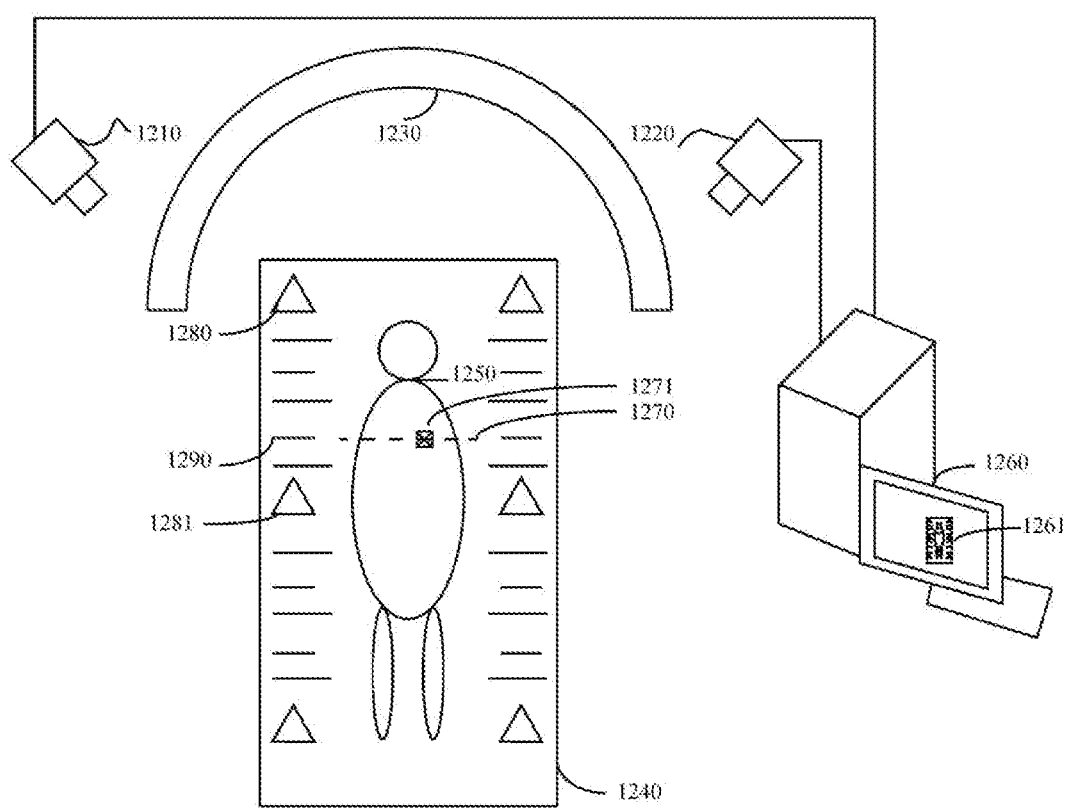
FIG. 12 illustrates an exemplary positioning procedure that is performed upon execution of the control information generated by the positioning system, according to some embodiments of the present disclosure.

FIG. 12 illustrates an exemplary positioning procedure that is performed upon execution of the control information generated by the positioning system, according to some embodiments of the present disclosure. Particularly, as shown in the figure, the imaging system comprises one or more cameras (1210, 1220), an imaging gantry 1230, a patient support 1240 and a display 1260. A patient 1250 lies on top of the patient support 1240. An image 1261 of the patient lying on the patient support is generated and shown on the display 1260.

Based on the displayed image, a system operator draws a line or an area across the displayed patient's chest, defining an edge of the ROI. For example, the system operator may draw an area 1721 on the displayed image. The positioning system 100 thus calculates corresponding physical position of the line 1270 and/or the area 1721, and generates control information for moving and positioning the patient support 1240 relative to other components of the imaging system.

In some embodiments, the positioning system may comprise one or more position markers. For example, as shown in the figure, a set of position markers may be placed on the surface of the patient support 1240. Additionally or alternatively, as shown in the figure, a position marker 1271 may be placed on the patient's body.

In some embodiments, these position markers may assist the system operator in defining the ROI by providing reference points. Particularly, the displayed image may show the patient's position relative to one or more position markers. If one or more position markers are placed on the edge of the ROI, the system operator may simply draws the line across the markers.

In some embodiments, these position markers may further assist the positioning system in generating control information. Particularly, physical locations of one or more position makers may be known to the positioning system. For example, in some embodiments, a position marker may be zero position 900 as described in relation to FIG. 9, with respect to which the ROI's physical location may be calculated. In some embodiments, physical locations of position markers may directly correspond to distances by which the patient support 1240 should be moved. For example, a set of rough and fine markers may function like a distance ruler, with the space between adjacent markers representing a distance of 10 centimeters. Thus, if the positioning system, via for example machine vision, recognizes that the line 1270 crosses the fourth fine marker 1290 between the first and second rough markers 1280 and 1281, the positioning system generates control information, which upon execution, would move the patient support 1240 inward of the imaging gantry 1250 by 40 centimeters.

According to the present disclosure, position markers that may be used in connection with the present disclosure may be of any combination of colors, shapes, and/or textures. Exemplary embodiments include black, white, gray scale, colorful, fluorescent; standard geometrical shapes such as circle, oval, triangle, square, trapezium, diamond, rhombus, parallelogram, rectangle, pentagon, hexagon, heptagon, oblong, octagon, nonagon, decagon or the like; symbols such as star, heart, moon, arrow, strip, ladder or the like; icons or images such as a teddy bear, a national flag or the like; letters, barcodes and characters; textures such as rough, smooth, heat-absorbing, heart-reflecting, etc.

Further, in some embodiments, one or more position markers may be integrated with components of the imaging system. In some embodiments, components of the imaging system having characteristic features may serve the function of a position marker. For example, a head coil for MRI scanning wore by a patient may serve as a position marker. The positioning system, upon recognizing the characteristic shape of the coil, would generate control information that positions the patient's head and the coil in a targeted area.

In some embodiments, the control information is executed by the positioning system or an external system that communicates with the positioning system (such as a HIS). In some embodiments, execution of the control information involves a system operator to initiate an execution command (such as pressing a button). In other embodiments, execution of the control information is performed automatically by the system without human intervention, when certain conditions are met (such as immediately after control information is generated).

In various embodiments, the system executes control information to perform a positioning procedure that moves and positions an imaging object and one or more components of the imaging system relative to one another, such that the ROI is targeted in the corresponding imaging session. Particularly, system components moved and positioned during the positioning procedure include but are not limited to a support (e.g., a patient bed, a handle etc.), a data acquisition device (e.g., an X-ray generator, a PET detector, etc.), a monitoring device (e.g., a camera, a lamp etc.), a communication device (e.g., a microphone, a keypad, etc.), and a mechanical part (e.g., for carrying the system components, for adjusting a patient position, etc.). In some embodiments, during the positioning procedure, the system sends voice instruction for a patient to perform.

It should be noted that the above examples are provided for the purposes of illustration, and not intended to limit the scope of the present disclosure. After consulting the present disclosure, one skilled in the art may envisage numerous other changes, substitutions, variations, alterations, and modifications without inventive activity, and it is intended that the present disclosure encompasses all such changes, substitutions, variations, alterations, and modifications as falling within its scope.

Figure 13:
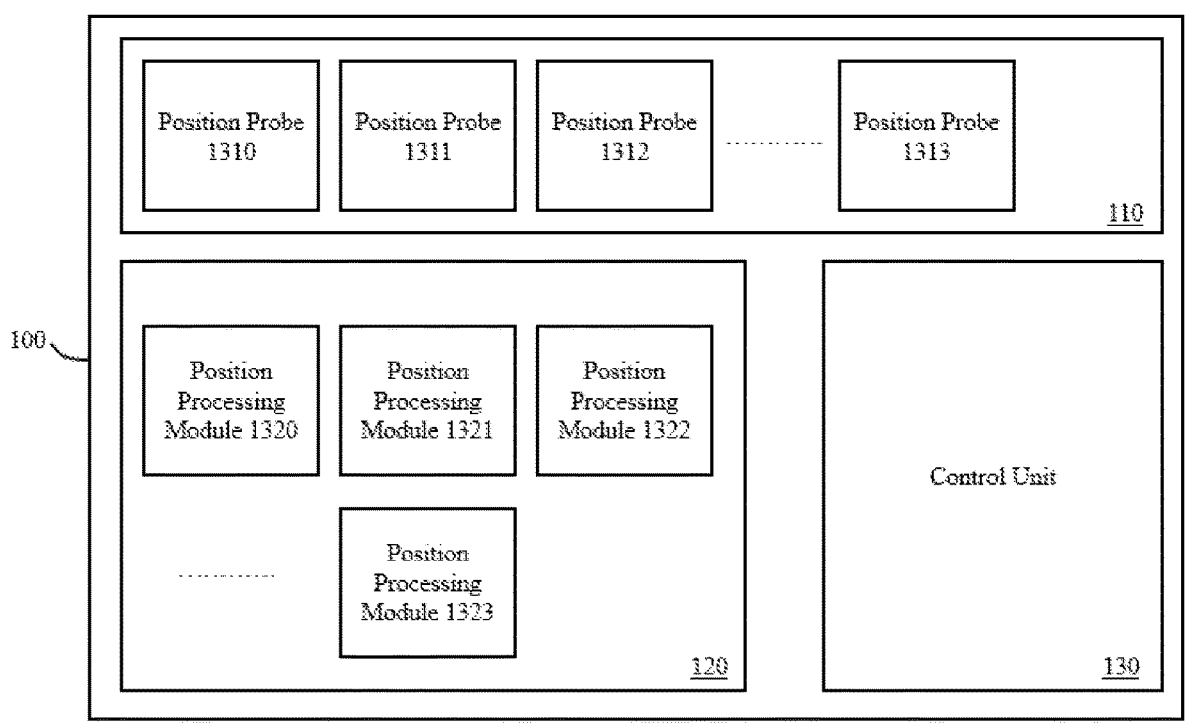
FIG. 13 is a block diagram of the positioning system according to some embodiments of the present disclosure.

FIG. 13 is a block diagram of the positioning system 100 according to some embodiments of the present disclosure. As shown in the figure, the positioning system 100 may comprise a position acquiring unit 110, a position processing unit 120, and a control unit 130 as described in connection with FIG. 1. Further, the position acquiring unit 110 may comprise one or more position probes, for example, position probe 1310, position probe 1311, position probe 1312, and position probe 1313. The position probes may be configured to communicate with one or more position sources.

The position processing unit 120 may comprise one or more position processing modules, for example, position processing module 1320, position processing module 1321, position processing module 1322, and position processing module 1323. The position processing module(s) may be configured to process the position information acquired by the position probe(s). Merely by way of example, the position of the position source(s) may be calculated by the position processing module(s). The control unit 130 may be configured to receive the position information calculated by the position processing unit 120, and control imaging system accordingly.

In some embodiments, ultrasound may be employed in the positioning system 100 to enable intercommunication between a position probe and a position source. For example, in some embodiments, the position source may be configured to emit ultrasound, and the position probe may be configured to receive the ultrasound signal. The distance between the position source and the position probe can be calculated based on the time delay between when the position source emits and when the position probe receives the signal. Thus, the position of a position source in a three-dimensional space may be calculated based on the distance between the position source and one or more position probes of known locations in the three-dimensional space, depending on relative spatial relationships between the position source and the position probe(s).

In some embodiments, the positioning system 100 may use alternative non-contact distance sensors to measure a distance between a position source and a position probe. For example, in some embodiments, infrared sensors or laser sensors may be used to measure the distance.

It should be noted that the description of the above embodiment of the positioning system is provided for the purposes of illustration, and not intended to limit the scope of the present disclosure. After consulting the present disclosure, one skilled in the art may envisage numerous other changes, substitutions, variations, alterations, and modifications without inventive activity, and it is intended that the present disclosure encompasses all such changes, substitutions, variations, alterations, and modifications as falling within its scope.

Figure 14:
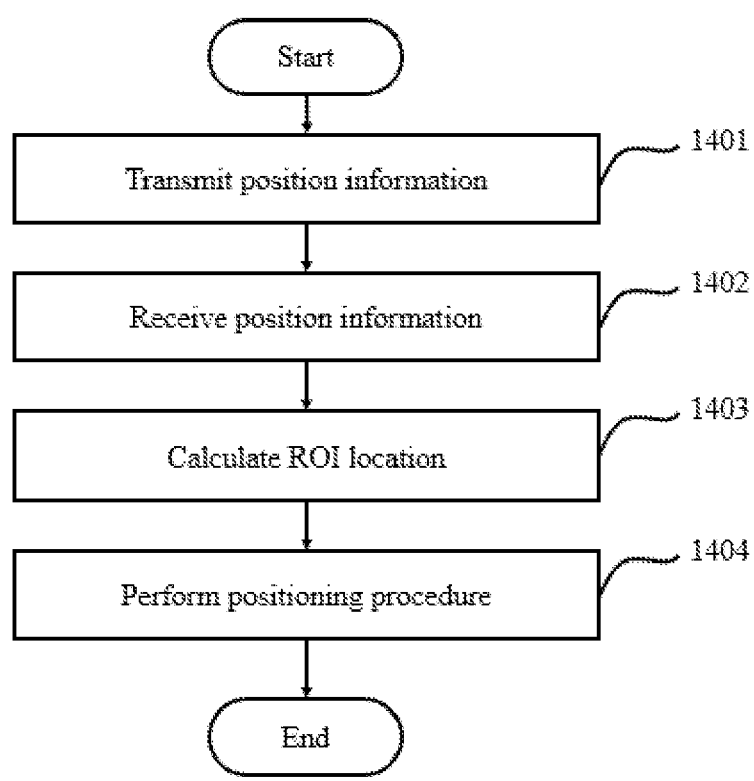
FIG. 14 is a flowchart illustrating an exemplary process of patient positioning according to some embodiments of the present disclosure.

FIG. 14 is a flowchart illustrating an exemplary process of patient positioning according to some embodiments of the present disclosure.

In step 1401, position information may be transmitted. The position information may be an ultrasound signal, a laser signal or an infrared signal, or the like, or any combination thereof.

In step 1402, the position information may be received. For example, in some embodiment, the position information may be received by an ultrasound sensor, a laser sensor or an infrared sensor, or the like, or any combination thereof.

In some embodiments, the positioning system may continuously monitor a patient's status by analyzing the position information. For example, in some embodiments, a position source may be placed on or near an ROI of a patient's body. Thus, the position information becomes indicative of the ROI's position. Accordingly, in some embodiments, in step 1403, the ROI's position may be calculated based on the position information received in step 1402. Merely by way of example, in some embodiments, location of a position source and thus the ROI can be calculated based on the distance between the position source and one or more position probes with known locations.

In step 1404, the imaging system may be controlled according to the ROI's position as calculated in step 1403. In some embodiments, the imaging system may be configured to monitor the status of a patient, including but not limited to monitoring the instant position of an ROI of the patient's body. In some embodiments, the positioning system may automatically adjust the location of the patient's body in real time, after the ROI's position is changed.

It should be noted the description above is provided for the purposes of illustration, and not intended to limit the scope of the present disclosure. After consulting the present disclosure, one skilled in the art may envisage numerous other changes, substitutions, variations, alterations, and modifications without inventive activity, and it is intended that the present disclosure encompasses all such changes, substitutions, variations, alterations, and modifications as falling within its scope.

Figure 15:
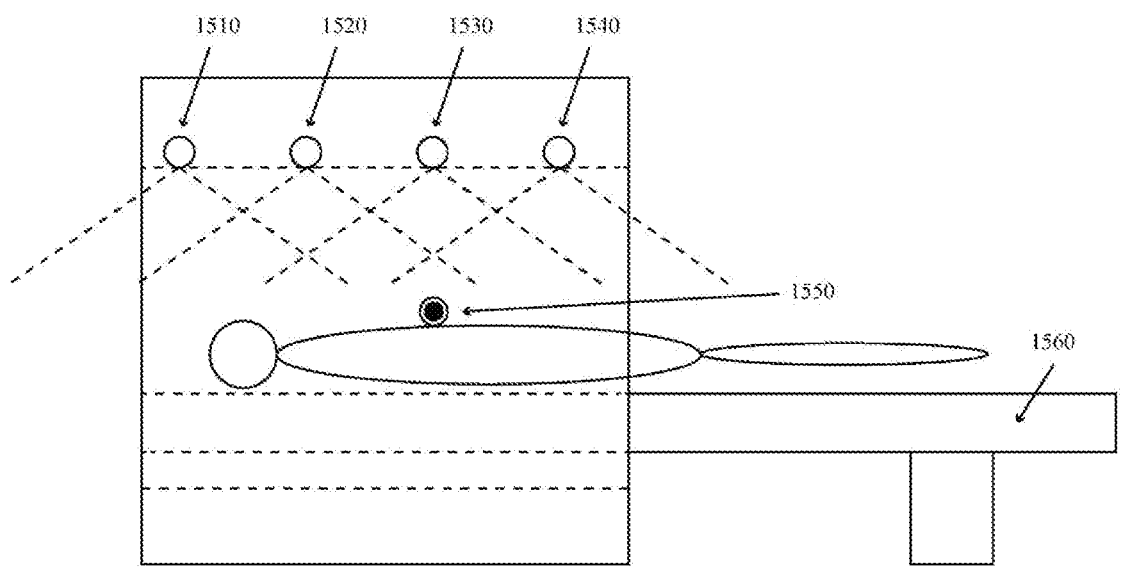
FIG. 15 is an illustration of the positioning system according to some embodiments of the present disclosure.

FIG. 15 is an illustration of the positioning system 100 according to some embodiments of the present disclosure. As shown in the figure, the positioning system 100 is equipped with multiple position probes (1510, 1520, 1530, 1540) for monitoring the status of a patient lying in the imaging system 1560. A position source 1550 is placed on the patient's body near a ROI that is to be targeted during imaging. The position source 1550 communicates with each of the position probes (1510, 1520, 1530, 1540) and the distance between the position source 1550 and each of the position probes (1510, 1520, 1540, 1540) can be measured.

Figure 16:
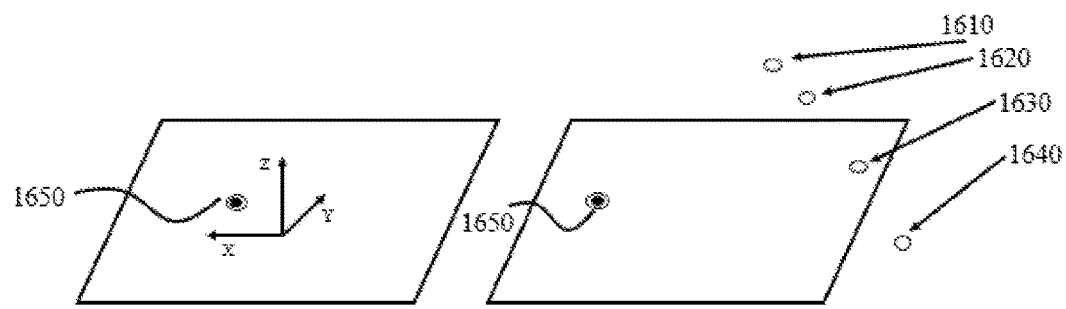
FIG. 16 illustrates a coordinate system that can be used to calculate the location of the position source in a three-dimensional space.

FIG. 16 illustrates a coordinate system that can be used to calculate the location of the position source 1650 in a three-dimensional space. As shown in the figure, set a xyz coordinate system where the position source 1650 can be treated as a point in the x-y plane. The multiple position probes (1610, 1620, 1630, 1640) can be treated as scattered points in the coordinate system, which may or may not in the x-y plane. In various embodiments, the multiple position probes (1610, 1620, 1630, 1640) may or may not share a same line or share a same plane in the xyz coordinate system.

Figure 17:
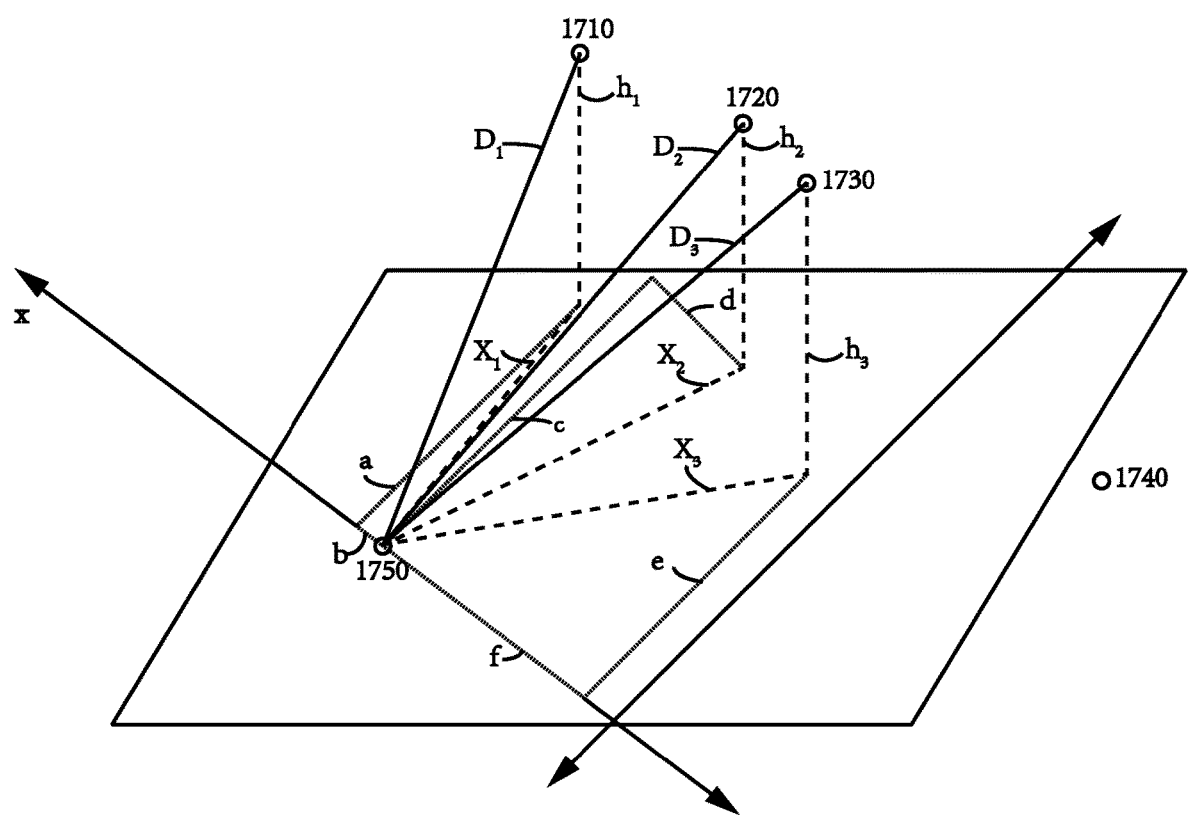
FIG. 17 illustrates one exemplary method for calculating the location of a position source in a three-dimensional space according to some embodiments of the present disclosure.

FIG. 17 illustrates one exemplary method for calculating the location of a position source in a three-dimensional space according to some embodiments of the present disclosure. As shown in the figure, the position source 1750 is in the x-y plane and may move along the x-axis. In various embodiments, one or more position probes (e.g., 1710, 1720, 1730, 1740) may assume various positional relationships with respect to the position source 1750 and/or with respect to one another. One or more of the position probes (e.g., 1710, 1720, 1730, 1740) may or may not locate in the x-y plane.

In the figure, $D_1$, $D_2$, and $D_3$ denote respectively the distance between the position source 1750 and each of the position probes (1710, 1720, 1730); $h_1$, $h_2$, $h_3$ denote respectively the distance between the x-y plane and each of the position probes (1710, 1720, 1730). $X_1$, $X_2$, and $X_3$ denote respectively the projection of $D_1$, $D_2$, and $D_3$ on the x-y plane; a, c, e denote respectively the y-axis component of $X_1$, $X_2$ and $X_3$; and b, d, f denote respectively the x-axis component $X_1$, $X_2$, and $X_3$. In some embodiments, a patient support as described in connection with FIG. 1 moves along the x-axis. Therefore, $$D_1^2 = a^2 + b^2 + h_1^2$$

$$D_2^2 = c^2 + d^2 + h_2^2$$

$$D_3^2 = e^2 + f^2 + h_3^2$$

$$c - a = \Delta_1$$

$$b + d = \Delta_2$$

$$b + f = \Delta_3$$

$$e - c = \Delta_4$$

$$h_1 - h_2 = \Delta_5$$

$$h_2 - h_3 = \Delta_6$$

$$h_3 - h_1 = \Delta_7 \quad \text{(Equation Set 1)}$$

where $\Delta_1$, $\Delta_2$, $\Delta_3$, $\Delta_4$, $\Delta_5$, $\Delta_6$, $\Delta_7$ are known design constants. By solving Equation Set 1, three-dimensional location of the position source 1750 can be obtained.

In some embodiments, the one or more position probes (e.g., 1710, 1720, 1730, 1740) may share a same plane which is in parallel with the x-y plane in the xyz coordinate system as described in connection with FIG. 16. Under this circumstance, $h_1$ may equal to $h_2$ and $h_2$ may equal to $h_3$. Thus $\Delta_5$, $\Delta_6$ and $\Delta_7$ all equal to 0.

In some embodiments, the perpendicular height to the x-y plane of the position probes (1710, 1720, 1730) may differ. In this case at least one of $\Delta_5$, $\Delta_6$, $\Delta_7$ is nonzero.

In some embodiments, during operation of the imaging system, location of the position source may be moved. In some embodiments, the positioning system is configured to measures $D_1$, $D_2$, and $D_3$ constantly, for example via ultrasound distance sensing. Thus, location of the position source 1750 may be monitored in real time.

In some embodiments, each position probe has a signal range, within which range it communicates with a position source. In some embodiments, the system automatically establishes communication between a moving position source and a position probe, once the source enters the signal range of the probe. In some embodiments, the system automatically terminates communication between a moving position source and a position probe, once the source leaves the signal range of the probe.

In some embodiments, multiple position probes are arranged such that their respective signal ranges overlap. Particularly, in some embodiments, when a moving position source leaves the signal range of a position probe, it simultaneously enters the signal range of another position probe. In some embodiments, the positioning system is configured to use different sets of location probes for monitoring the instant location of a moving position source. For example, as shown in FIG. 17, if position source 1750 moves towards position probe 1740 and away from position probe 1710, it may establish communication with probe 1740 while terminating communication with probe 1710. Accordingly, the positioning system would then calculate location of source 1750 based on known locations of probes 1720, 1730 and 1740.

It should be noted the description above is provided for the purposes of illustration, and not intended to limit the scope of the present disclosure. After consulting the present disclosure, one skilled in the art may envisage numerous other changes, substitutions, variations, alterations, and modifications without inventive activity, and it is intended that the present disclosure encompasses all such changes, substitutions, variations, alterations, and modifications as falling within its scope.

Having thus described the basic concepts, it may be rather apparent to those skilled in the art after reading this detailed disclosure that the foregoing detailed disclosure is intended to be presented by way of example only and is not limiting. Various alterations, improvements, and modifications may occur and are intended to those skilled in the art, though not expressly stated herein. These alterations, improvements, and modifications are intended to be suggested by this disclosure, and are within the spirit and scope of the exemplary embodiments of this disclosure.

Moreover, certain terminology has been used to describe embodiments of the present disclosure. For example, the terms "one embodiment," "an embodiment," and/or "some embodiments" mean that a particular feature, structure or characteristic described in connection with the embodiment is included in at least one embodiment of the present disclosure. Therefore, it is emphasized and should be appreciated that two or more references to "an embodiment" or "one embodiment" or "an alternative embodiment" in various portions of this specification are not necessarily all referring to the same embodiment. Furthermore, the particular features, structures or characteristics may be combined as suitable in one or more embodiments of the present disclosure.

Further, it will be appreciated by one skilled in the art, aspects of the present disclosure may be illustrated and described herein in any of a number of patentable classes or context including any new and useful process, machine, manufacture, or composition of matter, or any new and useful improvement thereof. Accordingly, aspects of the present disclosure may be implemented entirely hardware, entirely software (including firmware, resident software, micro-code, etc.) or combining software and hardware implementation that may all generally be referred to herein as a "block," "module," "engine," "unit," "component," or "system." Furthermore, aspects of the present disclosure may take the form of a computer program product embodied in one or more computer readable media having computer readable program code embodied thereon.

A computer readable signal medium may include a propagated data signal with computer readable program code embodied therein, for example, in baseband or as part of a carrier wave. Such a propagated signal may take any of a variety of forms, including electro-magnetic, optical, or the like, or any suitable combination thereof. A computer readable signal medium may be any computer readable medium that is not a computer readable storage medium and that may communicate, propagate, or transport a program for use by or in connection with an instruction execution system, apparatus, or device. Program code embodied on a computer readable signal medium may be transmitted using any appropriate medium, including wireless, wireline, optical fiber cable, RF, or the like, or any suitable combination of the foregoing.

Computer program code for carrying out operations for aspects of the present disclosure may be written in any combination of one or more programming languages, including an object oriented programming language such as Java, Scala, Smalltalk, Eiffel, JADE, Emerald, C++, C #, VB. NET, Python or the like, conventional procedural programming languages, such as the "C" programming language, Visual Basic, Fortran 2003, Perl, COBOL 2002, PHP, ABAP, dynamic programming languages such as Python, Ruby and Groovy, or other programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider) or in a cloud computing environment or offered as a service such as a Software as a Service (SaaS).

Furthermore, the recited order of processing elements or sequences, or the use of numbers, letters, or other designations therefore, is not intended to limit the claimed processes and methods to any order except as may be specified in the claims. Although the above disclosure discusses through various examples what is currently considered to be a variety of useful embodiments of the disclosure, it is to be understood that such detail is solely for that purpose, and that the appended claims are not limited to the disclosed embodiments, but, on the contrary, are intended to cover modifications and equivalent arrangements that are within the spirit and scope of the disclosed embodiments. For example, although the implementation of various components described above may be embodied in a hardware device, it may also be implemented as a software only solution—e.g., an installation on an existing server or mobile device.

Similarly, it should be appreciated that in the foregoing description of embodiments of the present disclosure, various features are sometimes grouped together in a single embodiment, figure, or description thereof for the purpose of streamlining the disclosure aiding in the understanding of one or more of the various inventive embodiments. This method of disclosure, however, is not to be interpreted as reflecting an intention that the claimed subject matter requires more features than are expressly recited in each claim. Rather, inventive embodiments lie in less than all features of a single foregoing disclosed embodiment.

What is claimed is:

1. A system for positioning a patient in an imaging system, the imaging system including at least one camera, the system comprising:
    at least one storage device storing a set of instructions; and
    at least one processor configured to communicate with the at least one storage device, wherein when executing the set of instructions, the at least one processor is configured to direct the system to perform operations including:
    acquiring, using the at least one camera, at least one image of the patient;
    determining, based on the at least one image, a posture of the patient;
    identifying a region of interest (ROI) of the patient from the at least one image; and
    generating, based on at least one of the posture or the identified ROI of the patient, control information of the imaging system for positioning the patient.

2. The system of claim 1, wherein the identifying an ROI of the patient from the at least one image comprises:
    determining whether the posture of the patient is consistent with a planned posture; and
    in response to determining that the posture of the patient is consistent with the planned posture, identifying the ROI of the patient from the at least one image.

3. The system of claim 1, wherein the generating, based on at least one of the posture or the identified ROI of the patient, control information of the imaging system for positioning the patient comprises:
    determining whether the posture of the patient is consistent with a planned posture; and
    in response to determining that the posture of the patient is consistent with the planned posture, generating the control information of the imaging system for positioning the patient based on the identified ROI of the patient.

4. The system of claim 1, wherein the posture of the patient includes at least one of a gesture feature or an orientation feature of the patient.

5. The system of claim 1, wherein the identifying an ROI of the patient from the at least one image includes:

extracting one or more body features from the at least one image; and identifying, based on the one or more body features, the ROI from the at least one segmented image.

6. The system of claim 1, wherein the patient is placed on a patient support, a first position marker is placed on the ROI, a second position mark with a known position is placed on the patient support, and the identifying an ROI of the patient from the at least one image includes:

identifying, from at least one image, the first position marker and the second position marker; and determining, based on the identified first position marker and the second position marker, a position of the ROI.

7. The system of claim 1, wherein the at least one camera includes a plurality of cameras having overlapping fields of view, the at least one image includes a plurality of images captured by the plurality of cameras, and the determining a posture of the patient based on the at least one image of the patient includes:

generating a panoramic image relating to the patient by composing the plurality of images; and determining, based on the panoramic image, the posture of the patient, wherein the identifying an ROI of the patient from the at least one image includes identifying the ROI of the patient from the panoramic image.

8. The system of claim 7, wherein the patient is placed on a patient support that includes a reference pattern, and the panoramic image relating to the patient is generated based on the reference pattern.

9. The system of claim 1, wherein the at least one camera includes:

a position source configured to transmit a positioning signal; and one or more position probes each of which is configured to receive the positioning signal from the position source.

10. The system of claim 9, wherein the positioning signal includes at least one of an ultrasound signal, an infrared signal, or a laser signal.

11. A method for positioning a patient in an imaging system, the imaging system including at least one camera, the method comprising:

acquiring, using the at least one camera, at least one image of the patient;

determining, based on the at least one image, a posture of the patient;

identifying a region of interest (ROI) of the patient from the at least one image; and generating, based on at least one of the posture or the identified ROI of the patient, control information of the imaging system for positioning the patient.

12. The method of claim 11, wherein the identifying an ROI of the patient from the at least one image comprises:

determining whether the posture of the patient is consistent with a planned posture; and in response to determining that the posture of the patient is consistent with the planned posture, identifying the ROI of the patient from the at least one image.

13. The method of claim 11, wherein the generating, based on at least one of the posture or the identified ROI of the patient, control information of the imaging system for positioning the patient comprises:

determining whether the posture of the patient is consistent with a planned posture; and in response to determining that the posture of the patient is consistent with the planned posture, generating the control information of the imaging system for positioning the patient based on the identified ROI of the patient.

14. The method of claim 11, wherein the posture of the patient includes at least one of a gesture feature or an orientation feature of the patient.

15. The method of claim 11, wherein the identifying an ROI of the patient from the at least one image includes:

extracting one or more body features from the at least one image; and identifying, based on the one or more body features, the ROI from the at least one segmented image.

16. The method of claim 11, wherein the patient is placed on a patient support, a first position marker is placed on the ROI, a second position mark with a known position is placed on the patient support, and the identifying an ROI of the patient from the at least one image includes:

identifying, from at least one image, the first position marker and the second position marker; and determining, based on the identified first position marker and the second position marker, a position of the ROI.

17. The method of claim 11, wherein the at least one camera includes a plurality of cameras having overlapping fields of view, the at least one image includes a plurality of images captured by the plurality of cameras, and the determining a posture of the patient based on the at least one image of the patient includes:

generating a panoramic image relating to the patient by composing the plurality of images; and determining, based on the panoramic image, the posture of the patient, wherein the identifying an ROI of the patient from the at least one image includes identifying the ROI of the patient from the panoramic image.

18. The method of claim 17, wherein the patient is placed on a patient support that includes a reference pattern, and the panoramic image relating to the patient is generated based on the reference pattern.

19. The method of claim 11, wherein the at least one camera includes:

a position source configured to transmit a positioning signal; and one or more position probes each of which is configured to receive the positioning signal from the position source.

20. A non-transitory computer readable medium, comprising a set of instructions for positioning a patient in an imaging system, the imaging system including at least one camera, wherein when executed by at least one processor, the set of instructions direct the at least one processor to effectuate a method, the method comprising:

acquiring, using the at least one camera, at least one image of the patient;

determining, based on the at least one image, a posture of the patient;

identifying a region of interest (ROI) of the patient from the at least one image; and generating, based on at least one of the posture or the identified ROI of the patient, control information of the imaging system for positioning the patient.

* * * * *